United States Patent [19]
Clark et al.

[11] Patent Number: 5,763,458
[45] Date of Patent: Jun. 9, 1998

[54] 1-PHENYLALKANONE 5-HT$_4$ RECEPTOR LIGANDS

[75] Inventors: Robin Douglas Clark, Palo Alto; Richard Malcolm Eglen; John Otis Gardner, both of Los Altos; Alam Jahangir, San Jose; Aaron Bayne Miller, Sunnyvale, all of Calif.

[73] Assignee: Syntex (U.S.A.) Inc., Palo Alto, Calif.

[21] Appl. No.: 456,168

[22] Filed: May 31, 1995

Related U.S. Application Data

[60] Division of Ser. No. 228,602, Apr. 26, 1994, abandoned, which is a continuation-in-part of Ser. No. 67,766, May 26, 1993, abandoned.

[51] Int. Cl.$^6$ ...................... A61K 31/445; C07D 211/32
[52] U.S. Cl. .......................... 514/318; 514/320; 546/196; 546/235
[58] Field of Search ............................ 514/318; 546/235

[56] References Cited

U.S. PATENT DOCUMENTS

| | | | |
|---|---|---|---|
| 3,957,823 | 5/1976 | Seebach et al. | 546/223 |
| 4,294,841 | 10/1981 | Champseix et al. | 424/267 |
| 5,116,846 | 5/1992 | Cain | 514/317 |

FOREIGN PATENT DOCUMENTS

| | | |
|---|---|---|
| 0 012 643 | 6/1980 | European Pat. Off. . |
| 0 063 075 | 10/1982 | European Pat. Off. . |
| 0 110 748 | 6/1984 | European Pat. Off. . |
| 0 201 775 | 11/1986 | European Pat. Off. . |
| 0 274 867 | 7/1988 | European Pat. Off. . |
| 0 449 186 | 10/1991 | European Pat. Off. . |
| 2 459 795 | 1/1981 | France . |
| 2 240 476 | 3/1992 | United Kingdom . |
| 94/07890 | 4/1994 | WIPO . |

OTHER PUBLICATIONS

Reynolds, "Prokinetic Agents: A Key in the Future of Gastroenterology", *Gastroenterology Clinics of North America*, 18: 437–457 (1989).

Corsi et al., "Pharmacological analysis of 5–hydroxtryptamine . . .", *Br. J. Pharmacol.*, 104: 719–725 (1991).

Kaumann et al., "A 5–HT$_4$–like receptor in human right atrium ", *Naunyn–Schmiedeberg's Arch. Pharmacol.*, 344: 150–159 (1991).

Frye et al., "Synthesis of 2–Aminobenzophenones . . . ", *J. Org. Chem.*, 56: 3750–3752 (1991).

Fieser et al., *Reagents for Organic Synthesis*, John Wiley & Sons, 8: 294–295 (1980).

Fieser et al., *Reagents for Organic Synthesis*, John Wiley & Sons, 1: 280 (1967).

Oster et al., "Acetylations of Strongly Basic . . . ", *Tetrahedron Lett.*, 24(18): 1851–1854 (1983).

Clark et al., *Principles of Psychopharmacology*, Academic Press, 166–167 (1970).

Tyers, "5–HT$_3$ Receptors", in Whitaker–Azmita et al., ed., *Ann. N. Y. Acad. Sci.*, 600: 195–196 (1990).

Turner et al., "Acylation of Ester Enolates . . . ", *J. Org. Chem.*, 54: 4229–4231 (1989).

Morrison and Boyd, *Organic Chemistry*, 3rd ed., Allyn and Bacon, 853–854 (1973).

Blum et al., "Design and Synthesis of Novel Ligands . . . ", *Bioorganic & Medicinal Chemistry Letters*, 2(5): 461–466 (1992).

"Silver halide color photographic material . . . ", abstract of Japanese Patent Kokai No. 241,306/1993 (Kokai published Sep. 21, 1993), *Chemical Abstracts*, 120(18): 993 (left column), Abstract 231861u (2 May 1994).

Clark et al. "Synthesis and preliminary pharmacological evaluation of 2–benzyloxy substituted aryl ketones as 5HT4 receptor antagonists" Bioorg. Med. Chem. Lett. v. 4 pp. 2481–2484, 1994.

Whitaker–Azmita et al. "The neuropharmacology of serotonin" N.Y. Aca. Sci. v. 600, pp. 194–196, 1990.

*Primary Examiner*—Ceila Chang
*Attorney, Agent, or Firm*—Heller Ehrman White & McAuliffe

[57] ABSTRACT

The present invention relates to novel 5-HT$_4$ receptor ligands which are 1-(5-halo-4-aminophenyl) (C$_{2-6}$)alkan-1-one derivatives in which the 5-halo-4-aminophenyl group is substituted at its 2-position with (C$_{1-4}$)alkyloxy or phenyl (C$_{1-4}$)alkyloxy and optionally substituted at its 3-position with (C$_{1-4}$)alkyloxy or substituted at its 2- and 3-positions together with methylenedioxy or ethylenedioxy and the highest numbered carbon of the (C$_{2-6}$)alkan-1-one is substituted with di(C$_{1-4}$)alkylamino, morpholin-1-yl or pyrrolidin-1-yl or optionally substituted piperidin-1-yl, piperidin-4-yl, azacyclohept-1-yl, azabicyclo[2.2.1]hept-3-yl, azabicylo[2.2.2]oct-3-yl or azabicylo[3.2.2]non-3-yl; and the pharmaceutically acceptable salts, individual isomers and mixtures of isomers and methods of using and making such derivatives.

22 Claims, No Drawings

1-PHENYLALKANONE 5-HT$_4$ RECEPTOR LIGANDS

This application is a division of application Ser. No. 08/228,602, filed Apr. 26, 1994, abandoned, which is in turn a continuation-in-part of application Ser. No. 08/067,766, filed May 26, 1993, abandoned.

BACKGROUND OF THE INVENTION

1. Field of the Invention:

This invention relates to novel 1-phenylalkan-1-one 5-HT$_4$ receptor ligands and the methods of using and preparing such ligands.

2. Description of the Field:

Serotonin, a neurotransmitter with mixed and complex pharmacological characteristics, was first discovered in 1948 and subsequently has been the subject of substantial research. Serotonin, also referred to as 5-hydroxytryptamine (5-HT), acts both centrally and peripherally on discrete 5-HT receptors. The 5-HT receptor is presently delineated into four major subclassifications-5-HT$_1$, 5-HT$_2$, 5-HT$_3$ and 5-HT$_4$ receptors - each of which may also be heterogeneous.

The 5-HT$_4$ receptor has been identified in a wide variety of tissue and species. For example, 5-HT$_4$ receptors have been identified in the central nervous system (e.g., autoradiographic studies show high specific binding of high affinity 5-HT$_4$ receptor ligands in olfactory tubercles, stratum, substantia nigra, and superior colliculus and dorsal, medial and ventral hippocampus). Thus, the 5-HT$_4$ receptor is thought to be involved in areas of the central nervous system affecting anxiety, depression, cognition, dependency, schizophrenia, appetite, etc., and drugs which interact with 5-HT$_4$ receptors (i.e., 5-HT$_4$ receptor ligands) have diverse therapeutic applications for central nervous system (CNS) disorders.

5-HT$_4$ Receptors are also found in the intestinal tracts of a wide variety of animal species, including man, and are found to modulate gastrointestinal motility (see Prokinetic Agents: A Key in the Future of Gastroenterology. Reynolds R. C. *Gastroenterology Clinics of North America* 1989, 18, 437–457).

In addition, 5-HT$_4$ receptors modulate smooth muscle tone of the urinary bladder (e.g., see Corsi, M.; Pietra, C.; Toson, G.; Trist, D.; Tuccitto, G.; Artibani, W. *Br. J. Pharmacol.* 1991, 104, 719–725) and also mediate 5-HT induced positive chronotropy in right atrial tissue (e.g., see Kaumann, A.; Sanders, L.; Brown, A.; Murray, K.; Brown, M.; Brown, M. *Naunyn-Schmiedeberg's.* 1991, 344, 150–159).

The disclosures of these and other documents referred to throughout this application (e.g., in the Pharmacology section of the Detailed Description of the Invention) are incorporated herein by reference.

SUMMARY OF THE INVENTION

The first aspect of the invention is a compound of Formula I:

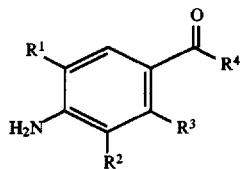

in which
R$^1$ is halo;
R$^2$ is hydrogen or (C$_{1-4}$)alkyloxy and R$^3$ is (C$_{1-4}$)alkyloxy or phenyl(C$_{1-4}$)alkyloxy (wherein the phenyl is optionally substituted with one to three substituents independently selected from halo, hydroxy, (C$_{1-4}$)alkyl, (C$_{1-4}$) alkyloxy, nitro, amino, aminocarbonyl, (C$_{1-4}$) alkylamino, di(C$_{1-4}$)alkylamino, (C$_4$)alkanoylamino and 3,4-methylenedioxy) or R$^2$ and R$^3$ together are methylenedioxy or ethylenedioxy; and R$^4$ is a group of Formula (a) or (b)

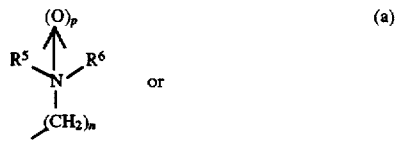

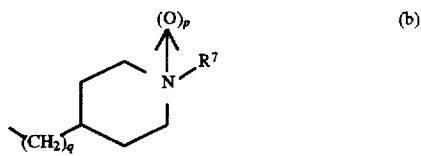

in which
n is 3, 4 or 5;
p is 0 or 1;
q is 1 or 2;
R$^5$ and R$^6$ are each (C$_{1-4}$)alkyl or together form —(CH$_2$)$_4$—, —(CH$_2$)$_6$—, —(CH$_2$)$_2$O(CH$_2$)$_2$— or —CHR$^8$CH$_2$CR$^9$R$^{10}$CHR$^{11}$CH$_2$— in which R$^8$ and R$^{11}$ are each hydrogen or together are —(CH$_2$)$_t$— in which t is 1, 2 or 3, R$^9$ is hydrogen, hydroxy, (C$_{1-8}$) alkyl, (C$_{3-8}$)alkenyl or (C$_{1-4}$)alkyloxy and R$^{10}$ is hydrogen, (C$_{1-8}$) alkyl or (C$_{3-8}$) alkenyl or phenyl, thienyl, pyrrolyl or furyl (optionally substituted with one to two substituents independently selected from (C$_{1-4}$)alkyl, (C$_{1-4}$)alkyloxy, trifluoromethyl and halo) or —(CH$_2$)$_x$R$^{12}$ in which x is 0, 1, 2 or 3 and R$^{12}$ is hydroxy, (C$_{1-4}$)alkyloxy, —C(O)NR$^{13}$R$^{14}$, —NR$^{13}$C (O)R$^{14}$, —NR$^{13}$C(O)OR$^{14}$, —SO$_2$NR$^{13}$R$^{14}$, —NR$^{13}$SO$_2$NR$^{14}$R$^{15}$ or —NR$^{13}$C(O)NR$^{14}$R$^{15}$ in which R$^{13}$, R$^{14}$ and R$^{15}$ are independently hydrogen, (C$_{1-4}$)alkyl, trifluoromethyl or aryl; and R$^7$ is hydrogen, (C$_{1-8}$)alkyl or (C$_{3-8}$)alkenyl or phenyl (C$_{1-4}$)alkyl (wherein the phenyl is optionally substituted with one to three substituents independently selected from (C$_{1-4}$)alkyloxy, methylenedioxy, ethylenedioxy or halo) or —(CH$_2$)$_z$R$^{12}$ in which z is 2 or 3 and R$^{12}$ is as defined above; and the pharmaceutically acceptable salts, individual isomers, and mixtures of isomers thereof.

A second aspect of this invention is a pharmaceutical composition comprising a therapeutically effective amount of a compound of Formula I, or of an individual isomer, a mixture of isomers, or the pharmaceutically acceptable salt or salts thereof, in combination with one or more pharmaceutically acceptable excipients.

A third aspect of this invention is a method for treating a condition capable of amelioration by drug interaction with 5-$HT_4$ receptors in an animal in need thereof, which method comprises administering to such animal a therapeutically effective amount of a compound of Formula I, or of an individual isomer, mixture of isomers, or the pharmaceutically acceptable salt or salts thereof.

A fifth aspect of this invention is the processes for preparing compounds of Formula I and is set forth in "Detailed Description of the Invention".

DETAILED DESCRIPTION OF THE INVENTION

Definitions:

Unless otherwise stated, the following terms used in the specification and claims have the meanings given below:

"Alkyl" means a straight or branched saturated hydrocarbon radical having from one to the number of carbon atoms designated (e.g., ($C_{1-4}$)alkyl includes the radicals methyl, ethyl, prop-1-yl, prop-2-yl, but-1-yl, but-2-yl, 2-methylpropyl and 2-methylprop-2-yl).

"Alkenyl" means a straight or branched unsaturated hydrocarbon radical having from 3 to the number of carbon atoms designated and in which the carbon atom with the free valence is saturated (e.g., ($C_{3-4}$)alkenyl includes the radicals 2-propenyl, 2-butenyl, 3-butenyl, 1-methyl-2-propenyl and 2-methyl-2-propenyl).

"Alkyloxy" means the radical —OR wherein R is alkyl having from one to the number of carbon atoms designated (e.g., ($C_{1-4}$)alkyloxy includes the radicals methoxy, ethoxy, prop-1-yloxy, prop-2-yloxy, but-1-yloxy, but-2-yloxy-, 2-methylprop-1-yloxy and 2-methylprop-2-yloxy).

"Alkanoyl" means the radical alkylcarbonyl having from one to the number of carbon atoms designated (e.g., ($C_{1-4}$) alkanoyl includes the radicals methanoyl, ethanoyl, propanoyl, butanoyl and 2-methylpropanoyl).

"Alkanoic acid or acid halide" means a straight saturated carboxylic acid or acid halide having 2 to 6 carbon atoms (e.g., acetic acid, propionic acid, butyric acid, valeric acid, hexanoic acid, acetyl chloride, propionyl chloride, etc.) and may refer to the substituted derivatives thereof.

"Alkanone or alkan-1-one" means a substituted straight saturated 1-ketone having from two to the number of carbon atoms designated (e.g., ($C_{2-6}$)alkan-1-one includes substituted ethan-1-one, propan-1-one, butan-1-one, pentan-1-one, and hexan-1-one).

"Aryl" means an organic radical derived from an aromatic hydrocarbon and includes monocyclic or condensed carbocyclic aromatic groups having from 6 to 20 carbon atoms (e.g., phenyl, naphthyl and the like).

"Halo" means fluoro, chloro, bromo or iodo.

"Leaving group" has the meaning conventionally associated with it in synthetic organic chemistry, i.e., an atom or group displaceable under alkylating conditions, and includes halo and alkane- or arenesulfonyloxy, such as mesyloxy, ethanesulfonyloxy, benzenesulfonyloxy and tosyloxy, and alkanesulfonylamino, alkanecarbonylamino, aminosufonylamino, aminocarbonylamino, and the like.

"Protective group" has the meaning conventionally associated with it in synthetic organic chemistry, i.e., a group which selectively blocks one reactive site in a multifunctional compound such that a chemical reaction can be carried out selectively at another unprotected reactive site.

"Deprotection" or "deprotecting" is the process by which a protective group is removed after the selective reaction is completed. Certain processes of this invention rely upon protective groups to block reactive nitrogen atoms present in the reactants. Acceptable amino protecting groups include acetyl and tert-butoxycarbonyl, which may be readily removed by acid hydrolysis.

"Animal" includes humans, non-human mammals, e.g., dogs, cats, rabbits, cattle, horses, sheep, goats, swine, and deer, and non-mammals, e.g., birds and the like.

"Disease" specifically includes any unhealthy condition of an animal or part thereof and includes an unhealthy condition which may be caused by, or incident to, medical or veterinary therapy applied to that animal, i.e., the "side effects" of such therapy.

"Optional" or "optionally" means that the subsequently described event or circumstance may or may not occur, and that the description includes instances where the event or circumstance occurs and instances in which it does not. For example, "optionally substituted with one to two substituents" means that the substituents may or may not be present in order for the compound described to fall within the invention, and the invention includes those compounds wherein one to two substituents are present and those compounds in which no substituents are present. "Pharmaceutically acceptable" means that which is useful in preparing a pharmaceutical composition that is generally safe, non-toxic and neither biologically nor otherwise undesirable and includes that which is acceptable for veterinary use as well as human pharmaceutical use. "Pharmaceutically acceptable salts" means salts which are pharmaceutically acceptable, as defined above, and which possess the desired pharmacological activity. Such salts include acid addition salts formed with inorganic acids such as hydrochloric acid, hydrobromic acid, sulfuric acid, nitric acid, phosphoric acid, and the like; or with organic acids such as acetic acid, propionic acid, hexanoic acid, heptanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 0-(4-hydroxybenzoyl)benzoic acid, cinnamic acid, mandelic acid, methanesulfonic acid, ethanesulfonic acid, 1,2,-ethanedisulfonic acid, 2-hydroxyethanesulfonic acid, benzenesulfonic acid p-chlorobenzenesulfonic acid, 2-naphthalenesulfonic acid, p-toluenesulfonic acid, camphorsulfonic acid, 4-methylbicyclo[2.2.2]oct-2-ene-1-carboxylic acid, glucoheptonic acid, 4,4'-methylenebis(3-hydroxy-2-ene-1-carboxylic acid), 3-phenylpropionic acid, trimethylacetic acid, tertiary butylacetic acid, lauryl sulfuric acid, gluconic acid, glutarnic acid, hydroxynaphthoic acid, salicylic acid, stearic acid, muconic acid, and the like.

Pharmaceutically acceptable salts also include base addition salts which may be formed when acidic protons present are capable of reacting with inorganic or organic bases. Acceptable inorganic bases include sodium hydroxide, sodium carbonate, potassium hydroxide, aluminum hydroxide and calcium hydroxide. Acceptable organic bases include ethanolamine, diethanolamine, triethanolamine, tromethamine, N-methylglucamine and the like.

"Therapeutically effective amount" means that amount which, when administered to an animal for treating a disease, is sufficient to effect such treatment for the disease.

"Treating" or "treatment" of a disease includes:

(1) preventing the disease from occurring in an animal which may be predisposed to the disease but does not yet experience or display symptoms of the disease, (2) inhibiting the disease, i.e., arresting its development, or (3) relieving the disease, i.e., causing regression of the disease.

The compounds of Formula I are named in accordance with acceptable nomenclature rules generally consistent with "Chemical Abstracts". For example, the compound of Formula I in which $R^1$ is chloro, $R^3$ is methoxy and $R^4$ is a group of Formula (a), in which n is 4, p is 0, and $R^5$ and $R^6$ are each methyl

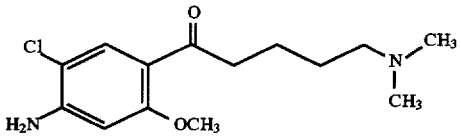

is named 1-(4-amino-5-chloro-2-methoxyphenyl)-5-dimethylaminopentan-1-one.

Presently Preferred Embodiments:

The compounds of this invention are $(C_{2-6})$alkan-1-ones derivatives having a substituted phenyl moiety at the 1-position and a nitrogen containing moiety at the highest numbered position. The nitrogen containing moiety may be (N,N-disubstituted)amino, (1-substituted)piperidin-4-yl, morpholin-1-yl or pyrrolidin-1-yl or optionally substituted piperidin-1-yl, azacyclohept-1-yl, azabicyclo[2.2.1]hept-3-yl, azabicylo[2.2.2]oct-3-yl or azabicylo[3.2.2]non-3-yl.

Compounds of Formula I in which $R^2$ is hydrogen, $R^3$ is $(C_{1-4})$ alkyloxy and $R^4$ is a group of Formula (a) are designated compounds of Formula I(a):

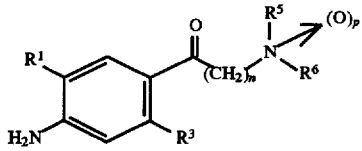

in which n is 3, 4 or 5;

p is 0 or 1;

$R^1$ is halo; and $R^5$ and $R^6$ are each $(C_{1-4})$alkyl or together form $-(CH_2)_4-$, $-(CH_2)_6-$, $-(CH_2)_2O(CH_2)_2-$ or $-CHR^8CH_2CR^9R^{10}CHR^{11}CH_2-$ in which $R^8$ and $R^{11}$ are each hydrogen or together are $-(CH_2)_4-$ in which t is 1, 2 or 3, $R^9$ is hydrogen, hydroxy, $(C_{1-8})$ alkyl, $(C_{3-8})$alkenyl or $(C_{1-4})$alkyloxy, and $R^{10}$ is hydrogen, $(C_{1-8})$alkyl or $(C_{3-8})$alkenyl or phenyl, thienyl, pyrrolyl or furyl (optionally substituted with one to two substituents independently selected from $(C_{1-4})$ alkyl, $(C_{1-4})$ alkyloxy, trifluoromethyl, and halo) or $-(CH_2)_xR^{12}$ in which x is 0, 1, 2 or 3 and $R^{12}$ is hydroxy, $(C_{1-4})$alkyloxy, $-C(O)NR^{13}R^{14}$, $-NR^{13}C(O)R^{14}$, $-NR^{13}C(O)OR^{14}$, $-SO_2NR^3R^{14}$, $-NR^{13}SO_2R^{14}$, $-NR^{13}SO_2NR^{14}R^{15}$ or $-NR^{13}C(O)NR^{14}R^{15}$ in which $R^{13}$, $R^{14}$ and $R^{15}$ are independently hydrogen, $(C_{1-4})$alkyl or trifluoromethyl; and the pharmaceutically acceptable salts, individual isomers, and mixtures of isomers thereof.

Compounds of Formula I which $R^2$ is hydrogen or $(C_{1-4})$alkyloxy and $R^3$ is $(C_{1-4})$alkyloxy or $R^2$ and $R^3$ together are methylenedioxy or ethylenedioxy and $R^4$ is a group of Formula (b) are designated as compounds of Formula I(b):

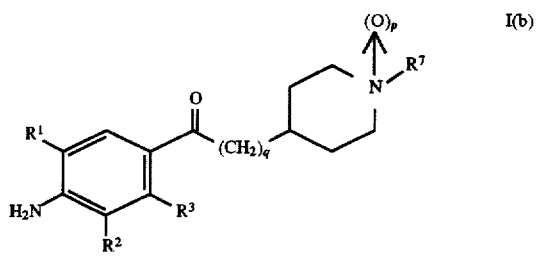

in which p is 0 or 1;

q is 1 or 2;

$R^1$ is halo; and $R^7$ is hydrogen, $(C_{1-8})$alkyl, $(C_{3-8})$alkenyl or phenyl $(C_{1-4})$alkyl (wherein the phenyl is optionally substituted with one to three substituents independently selected from $(C_{1-4})$alkyloxy, methylenedioxy, ethylenedioxy or halo) or $-(CH_2)_zR^{12}$ in which z is 2 or 3 and $R^{12}$ is hydroxy, $(C_{1-4})$alkyloxy, $-C(O)NR^{13}R^{14}$, $-NR^{13}C(O)R^{14}$, $-NR^{13}C(O)OR^{14}$, $-SO_2NR^{13}R^{14}$, $-NR^{13}SO_2R^{14}$, $-NR^{13}SO_2NR^{14}R^{15}$ or $-NR^{13}C(O)NR^{14}R^{15}$ in which $R^{13}$, $R^{14}$ and $R^{15}$ are independently hydrogen, $(C_{1-4})$alkyl, trifluoromethyl or aryl; and the pharmaceutically acceptable salts, individual isomers, and mixtures of isomers thereof.

Compounds of Formula I in which $R^2$ is hydrogen and $R^3$ is $(C_{1-4})$alkylphenyloxy (wherein the phenyl is optionally substituted with one to three substituents independently selected from halo, hydroxy, $(C_{1-4})$alkyl, $(C_{1-4})$alkyloxy, nitro, amino, aminocarbonyl, $(C_{1-4})$ alkylamino, di $(C_{1-4})$ alkylamino, $(C_{1-4})$ alkanoylamino and 3,4-methylenedioxy) are designated as compounds of Formula I(c):

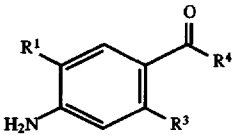

in which $R^1$ is halo; and $R^4$ is a group of Formula (a) or (b):

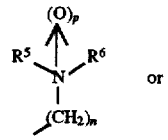

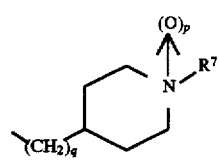

in which n is 3, 4 or 5;

p is 0 or 1;

q is 1 or 2;

$R^5$ and $R^6$ are each $(C_{1-4})$alkyl or together form $-(CH_2)_4-$, $-(CH_2)_6-$, $-(CH_2)_2O(CH_2)_2-$ or $-CHR^8CH_2CR^9R^{10}CHR^{11}CH_2-$ in which $R^8$ and $R^{11}$ are each hydrogen or together are $-(CH_2)_t-$ in which t is 1, 2 or 3, $R^9$ is hydrogen, hydroxy, $(C_{1-8})$ alkyl, $(C_{3-8})$allcenyl or $(C_{1-4})$alkyloxy and $R^{10}$ is hydrogen, $(C_{1-8})$alkyl or $(C_{3-8})$alkenyl or phenyl, thienyl, pyrrolyl or furyl (optionally substituted with one to two substituents independently selected from $(C_{1-4})$ alkyl, $(C_{1-4})$ alkyloxy, trifluoromethyl and halo) or —$(CH_2)_xR^{12}$ in which x is 0, 1, 2 or 3 and $R^{12}$ is hydroxy, $(C_{1-4})$alkyloxy, —$C(O)NR^{13}R^{14}$, —$NR^{13}C(O)R^{14}$, —$NR^{13}C(O)$ $OR^{14}$, —$SO_2NR^{13}R^{14}$, —$NR^{13}SO_2R^{14}$, —$NR^{13}SO_2NR^{14}R^{15}$ or —$NR^{13}C(O)NR^{14}R^{15}$ in which $R^{13}$, $R^{14}$ and $R^{15}$ are independently hydrogen, $(C_{1-4})$alkyl or trifluoromethyl; and $R^7$ is hydrogen, $(C_{1-8})$alkyl or $(C_{3-8})$alkenyl or phenyl$(C_{1-4})$alkyl (wherein the phenyl is optionally substituted with one to three substituents independently selected from $(C_{1-4})$alkyloxy, methylenedioxy, ethylenedioxy or halo) or —$(CH_2)_zR^{12}$ in which z is 2 or 3 and $R^{12}$ is as defined above; and the pharmaceutically acceptable salts, individual isomers, and mixtures of isomers thereof.

While the breadth of compounds which are intended by the invention is as set forth in the Summary of the Invention, certain compounds are preferred. For example, preferred compounds are compounds of Formula I(a) in which n is 4 and $R^5$ and $R^6$ together form —$CHR^8CH_2CR^9R^{10}CHR^{11}CH_2$—; and compounds of Formula I(b) in which q is 2; and compounds of Formula I(c) in which $R^4$ is a group of Formula (a) wherein n is 4 and $R^5$ and $R^6$ together form —$CHR^8CH^2CR^9R^{10}CHR^{11}CH_2$— or in which $R^4$ is a group of Formula I(b) wherein q is 2.

Particularly preferred are compounds of Formula I(a) in which n is 4, $R^1$ is chloro, $R^3$ is methoxy, and $R^5$ and $R^6$ together form —$CH_2CH^2CHR^{10}CH_2CH_2$— wherein $R^{10}$ is hydrogen, $(C_{1-8})$alkyl or —$(CH_2)^xR^{12}$; and compounds of Formula I(b) in which q is 2, $R^1$ is chloro, $R^3$ is methoxy, and $R^7$ is hydrogen, $(C_{1-8})$alkyl or —$(CH_2)_zR^{12}$; and compounds of Formula I(c) in which $R^1$ is chloro, $R^3$ is 3,5-dimethoxybenzyloxy, and $R^4$ is a group of Formula (a) wherein n is R4 and $R^5$ and $R^6$ together form —$CH_2CH_2CHR^{10}CH_2CH_2$— wherein $R^{10}$ is hydrogen, $(C_{1-8})$alkyl or —$(CH_2)_xR^{12}$ or $R^4$ is a group of Formula (b) wherein q is 2 and $R^7$ is hydrogen, $(C_{1-8})$alkyl or —$(CH_2)_zR^{12}$.

Most preferred are the following compounds of Formula I(a):

1-(4-amino-5-chloro-2-methoxy-phenyl)-5-(piperidin-1-yl)pentan-1-one, 1-(4-amino-5-chloro-2-methoxyphenyl)-5-(4-methylpiperidin-1-yl)pentan-1-one, 1-(4-amino-5-chloro-2-methoxyphenyl)-5-(4-aminocarbonylpiperidin-1-yl)-pentan-1-one, 1-(4-amino-5-chloro-2-methoxyphenyl)-5-{4-[(methylsulfonyl)amino]piperidin-1-yl}pentan-1-one; and the following compounds of Formula I(b):

1-(4-amino-5-chloro-2-methoxyphenyl)-3-(1-methylpiperidin-4-yl)propan-1-one, 1-(4-amino-5-chloro-2-methoxyphenyl)-3-(1-ethylpiperidin-4-yl)propan-1-one, 1-(4-amino-5-chloro-2-methoxyphenyl)-3-[1-(prop-1-yl)piperidin-4-yl]propan-1-one, 1-(4-amino-5-chloro-2-methoxyphenyl)-3-[1-(but-1-yl)piperidin-4-yl]propan-1-one, 1-(4-amino-5-chloro-2-methoxyphenyl)-3-[1-(pent-1-yl)piperidin-4-yl]propan-1-one, 1-(4-amino-5-chloro-2-methoxyphenyl)-3-{1-[2-(methylsulfonyl)aminoethyl]piperidin-4-yl}propan-1-one, 1-(4-amino-5-chloro-2-methoxyphenyl)-3-{1-[2-(dimethylaminosulfonyl)aminoethyl]piperidin-4-yl}propan-1-one!, 1-(4-amino-5-chloro-2-methoxyphenyl)-3-{1-[3-(methylsulfonyl)aminoprop-1-yl]piperidin-4-yl}propan-1-one;

1-(4-amino-5-chloro-2,3-dimethoxyphenyl)-3-[1-(3-butyl-1-yl)piperidin-4-yl]propan-1-one;

1-(4-amino-5-chloro-2,3-ethylenedioxyphenyl)-3-[1-(3-butyl-1-yl)piperidin-4-yl]propan-1-one;

1-(4-amino-5-chloro-2-methoxyphenyl)-3-{1-[3-(4-methoxyphenyl)prop-1-yl]piperidin-4-yl}propan-1-one;

1-(4-amino-5-chloro-2-methoxyphenyl)-3-{1-[3-(2,3,4-trimethoxyphenyl)prop-1-yl]piperidin-4-yl}propan-1-one;

1-(4-amino-5-chloro-2-methoxyphenyl)-3-{1-[3-(3,4-methylenedioxyphenyl)prop-1-yl]piperidin-4-yl}propan-1-one;

1-(4-amino-5-chloro-2-methoxyphenyl)-3-{1-[3-(3,4-ethylenedioxyphenyl)prop-1-yl]piperidin-4-yl}propan-1-one;

1-(4-amino-5-chloro-2-methoxyphenyl)-3-{1-[3-(3,4-dimethoxyphenyl)prop-1-yl]piperidin-4-yl}propan-1-one;

1-(4-amino-5-chloro-2-methoxyphenyl) -3-{1-[3-(3,5-dimethoxyphenyl)prop-1-yl]piperidin-4-yl}propan-1-one;

1-(4-amino-5-chloro-2,3-ethylenedioxyphenyl)-3-{1-[3-(4-methoxyphenyl)prop-1-yl]piperidin-4-yl}propan-1-one; and the following compounds of Formula I(c):

1-[4-amino-5-chloro-2-(3,5-dimethoxybenzyloxy)phenyl]-5-(piperidin-1-yl)pentan-1-one, 1-[4-amino-5-chloro-2-(3,5-dimethoxybenzyloxy)phenyl]-5-(4-methylpiperidin-1-yl)pentan-1-one, 1-[4-amino-5-chloro-2-(3,5-dimethoxybenzyloxy)phenyl]-5-[4-(prop-1-yl)piperidin-1-yl]pentan-1-one, 1-[4-amino-5-chloro-2-(3,5-dimethoxybenzyloxy)phenyl]-5-{4-[2-(methylsulfonyl)aminoethyl]piperidin-1-yl}pentan-1-one, 1-[4-amino-5-chloro-2-(3,5-dimethoxybenzyloxy)phenyl]-5-[4-(methylsulfonyl)aminomethylpiperidin-1-yl]pentan-1-one, 1-[4-amino-5-chloro-2-(3,5-dimethoxybenzyloxy)phenyl]-5-[4-(aminocarbonyl)aminomethylpiperidin-1-yl]pentan-1-one, 1-[4-amino-5-chloro-2-(3,5-dimethoxybenzyloxy)phenyl]-5-(4-aminocarbonylpiperidin-1-yl)pentan-1-one, 1-[4-amino-5-chloro-2-(3,5-dimethoxybenzyloxy)phenyl]-5-(4-hydroxypiperidin-1-yl)pentan-1-one, 1-[4-amino-5-chloro-2-(3,5-dimethoxybenzyloxy)phenyl]-5-(4-methoxypiperidin-1-yl)pentan-1-one, 1-[4-amino-5-chloro-2-(3,5-dimethoxybenzyloxy)phenyl]-5-[4-(aminocarbonyl)aminopiperidin-1-yl]pentan-1-one, 5 1-[4-amino-5-chloro-2-(3,5-dimethoxybenzyloxy)phenyl]-5-[4-(methylsulfonyl)aminopiperidin-1-yl]pentan-1-one, 1-[4-amino-5-chloro-2-(3,5-dimethoxybenzyloxy)phenyl]-3-[1-(but-1-yl)piperidin-4-yl]propan-1-one, 1-[4-amino-5-chloro-2-(3,5-dimethoxybenzyloxy)phen yl]-10 3-[1-(pent-1-yl)piperidin-4-yl]propan-1-one, 1-[4-amino-5-chloro-2-(3,5-dimethoxybenzyloxy)phenyl]-3-{1-[2-(methylsulfonyl)aminoethyl]piperidin-4-yl}propan-1-one; or the pharmaceutically acceptable salts, preferably the hydrochloride salts, thereof.

Pharmacology and Utility:

The compounds of the invention interact with 5-HT$_4$ receptors (i.e., the compounds have affinity for 5-HT$_4$ receptors and exhibit agonist or antagonist properties). The 5-HT$_4$ receptor interactant properties of test compounds are identified by an assay which utilizes rat, isolated thoracic esophageal muscle (i.e., test compounds which intrinsically produce relaxation are characterized as 5-HT$_4$ receptor agonists, while test compounds which inhibit agonist-induced, 5-HT$_4$ receptor mediated relaxation responses are characterized as 5-HT$_4$ receptor antagonists). The rat, isolated thoracic esophagus muscle is well established as a model for identifying and characterizing compounds that interact with 5-HT$_4$ receptors (e.g., see Baxter, G. S.; Craig, D. A.; Clarke, D. E. *Maunyn-Schmiedeberg's Arch. Pharmacol.* 1991, 343, 439–446) and is described in Example 17.

As 5-HT$_4$ receptor ligands, the compounds of this invention are useful for treating conditions which can be ameliorated by interaction with 5-HT$_4$ receptors. Such conditions include CNS disorders, gastrointestinal disorders, cardiovascular disorders, and urinary tract disorders.

Particular CNS disorders include a variety of neurologic and psychiatric disorders such as cognitive disorders, psychoses, and obsessive/compulsive and anxiety/depression behavior. Cognitive disorders include attentional or memory deficit, dementia states (including senile dementia of the Alzheimer's type and aging), cerebral vascular deficiency and Parkinson's disease. Psychoses which may be treatable with the compounds of this invention include paranoia, schizophrenia and autism. Obsessive/compulsive behavior includes eating disorders (e.g., bulimia, a condition in which an abnormal and constant: craving for food is present). Anxiety/depressive states include anticipatory anxiety (e.g., prior to surgery, dental work, etc.), depression, mania, seasonal affective disorder (SAD), and the convulsions and anxiety caused by withdrawal from addictive substances such as opiates, benzodiazapines, nicotine, alcohol, cocaine and other drugs of abuse.

Particular intestinal disorders include diseases which relate directly or indirectly to gastromotility of the stomach, esophagus and of both the large and small intestines. Specific diseases include, but are not limited to, dyspepsia (e.g., non-ulcer dyspepsia), gastric stasis, peptic ulcer, reflux esophagitis, flatulence, bile reflux gastritis, pseudo-obstruction syndrome, irritable colon syndrome (which may result in chronic constipation and diarrhea), diverticular disease, biliary dysmotility (which may result in sphincter of Oddi dysfunction and "sludge" or microscopic crystals in the gall bladder), gastroparesis (e.g., diabetic, postsurgical or idiopathic), irritable bowel syndrome and retarded gastric emptying. Other uses include short-term prokinesis to facilitate diagnostic radiology and intestinal intubation and for treating diarrhea, particularly diarrhea induced by cholera and carcinoid syndrome.

Particular cardiovascular disorders include diseases which relate directly or indirectly to cardiac arrhythmias. Particular urinary tract disorders include diseases which relate directly or indirectly to dysfunction of urinary smooth muscle or innervation causing inadequate urinary storage or control or urinary stasis and which may result in infection, calculi or renal damage.

In general, the particular condition that a compound of this invention may be useful in treating will depend upon whether the compound exhibits agonist qualities or antagonists qualities. For example, certain compounds of this invention which are 5-HT$_4$ receptor agonists are useful as prokinetic agents in treating diseases in which gastric motility is impaired or for enhancing ureteral smooth muscle tone in treating urinary tract diseases in which the bladder is hypotonic or as cognition enhancing agents for treating conditions which directly or indirectly relate to cognition deficit. In contrast, the compounds which are 5-HT$_4$ receptor antagonists can block 5-HT$_4$ receptor mediated peristalsis and are useful in treating diseases involving hypermotility states or can block 5-HT$_4$ receptor mediated contractions of ureteral smooth muscle and are useful in the treatment of diseases involving spasticity of the bladder or can block 5-HT$_4$ receptor mediated positive chronotropy and are useful as antiarrhythmic agents.

While the condition for which any given compound of this invention may be useful largely depends upon the antagonist or agonist qualities of the given compound, certain individual variations may occur. Thus, the 5-HT$_4$ receptor ligands of this invention may be further tested by in vivo or in vitro methodologies designed to determine therapeutic activity. For example, the prokinetic activity of compounds of this invention can be determined by measuring the increase in rate of gastric emptying in rats after oral administration of test compound. The rat, prokinetic assay is a well established model for identifying compounds that possess prokinetic activity (e.g., see Droppleman, D.; Gregory, R.; Alphin, R. S. *J. Pharmacol. Methods* 1980, 4(3), 227–30) and is described in Example 18.

The cognitive enhancing properties of compounds of this invention can be determined by using the Morris Water Maze Assay, which measures changes in the cognitive performance of rats. The Morris Water Maze Assay is a well established model for demonstrating cognition enhancing activity (e.g., see Morris, R. G. M.; Garrud, P.; Rawlins, J. N. P.; O'Keefe, J. *Nature.* 1982, 297, 681–683) and is described in Example 21.

Anxiolytic activity is determined by the art-recognized Crawley and Goodwin two-compartment exploratory model (e.g., see Kilfoil, T.; Michel, A.; Montgomery, D.; Whiting, R. L. *Neuropharmacology* 1989, 28(9), 901–905). In brief, the method measures the extent a compound affects the natural anxiety of mice in a novel, brightly lighted area. The anxiolytic behavior assay is described in Example 19.

Anxiolytic activity during withdrawal from drugs of abuse is determined by the mouse, withdrawal anxiety test, an accepted assay (e.g., see Carboni, E.; Acquas, E.; Leone, P.; Perezzani, L.; Di Chiara, G. *Eur. J. Pharsacol* 1988, 151, 159–160). This procedure utilizes the exploratory model described above to measure the extent a compound ameliorates the symptoms of withdrawal that occur after chronically treating with an addictive substance and then abruptly ceasing the treatments. The withdrawal anxiety assay is described in Example 20.

In summary, the compounds of this invention are useful for treating conditions which can be ameliorated by interaction with 5-HT$_4$ receptors. Such conditions include CNS disorders, gastrointestinal disorders, cardiovascular disorders, and urinary tract disorders. In particular, the compounds are useful for treating conditions relating to cognitive disorders, gastric hypomotility, irritable bowel syndrome, arrhythmia, hypotonicity of the bladder, or spasticity of the bladder.

Administration and Pharmaceutical Composition:

In general, compounds of the invention will be administered in therapeutically effective amounts via any of the usual and acceptable modes known in the art, either singly or in combination with another compound of Formula I or with another therapeutic agent. A therapeutically effective amount may vary widely depending on the severity of the disease, the age and relative health of the subject, the potency of the compound used and other factors. A therapeutically effective amount may range from approximately 0.01 milligram per Kg (mg/Kg) body weight per day to 10 mg/Kg body weight per day. Preferably the amount will be approximately 0.1 to 1 mg/Kg/day. Therefore, a therapeutically effective amount for a 70 Kg human may range from 0.7 to 700 mg/day, preferably 7 to 70 mg/day.

One of ordinary skill in the art of treating such diseases will be able, without undue experimentation and in reliance upon personal knowledge and the disclosure of this application, to ascertain a therapeutically effective amount of a compound of Formula I for a given disease.

In general, compounds of the invention will be administered as pharmaceutical compositions by one of the following routes: oral, systemic (e.g., transdermal, intranasal or by suppository) or parenteral (e.g., intramuscular, intravenous or subcutaneous). Compositions can take the form of tablets, pills, capsules, semisolids, powders, sustained release formulations, solutions, suspensions, elixirs, aerosols, or any other appropriate composition and are comprised of, in general, a compound of Formula I in combination with at least one pharmaceutically acceptable excipient. Acceptable excipients are non-toxic, aid administration, and do not adversely affect the therapeutic benefit of the compound of Formula I. Such excipient may be any solid, liquid, semisolid or, in the case of an aerosol composition, gaseous excipient that is generally available to one of skill in the art.

Solid pharmaceutical excipients include starch, cellulose, talc, glucose, lactose, sucrose, gelatin, malt, rice, flour, chalk, silica gel, magnesium stearate, sodium stearate, glycerol monostearate, sodium chloride, dried skim milk, and the like. Liquid and semisolid excipients may be selected from water, ethanol, glycerol, propylene glycol and various oils, including those of petroleum, animal, vegetable or synthetic origin (e.g., peanut oil, soybean oil, mineral oil, sesame oil, etc.). Preferred liquid carriers, particularly for injectable solutions, include water, saline, aqueous dextrose and glycols.

Compressed gases may be used to disperse the compound of the invention in aerosol form. Inert gases suitable for this purpose are nitrogen, carbon dioxide, nitrous oxide, etc. Other suitable pharmaceutical carriers and their formulations are described in A. R. Alfonso *Remington's Pharmaceutical Sciences* 1985, 17th ed. Easton, Pa.: Mack Publishing Company.

The amount of a compound of the invention in the composition may vary widely depending upon the type of formulation, size of a unit dosage, kind of excipients and other factors known to those of skill in the art of pharmaceutical sciences. In general, the final composition will comprise from 25% w to 75% w of the compound of Formula I, preferably 30% w to 50% w, with the remainder being the excipient or excipients.

Preferably the pharmaceutical composition is administered in a single unit dosage form for continuous treatment or in a single unit dosage form ad libitum when relief of symptoms is specifically required. Representative pharmaceutical formulations containing a compound of Formula I are described in Example 16.

Processes for Preparing Compounds of the Invention:

A method for making compounds of Formula I is depicted by the following Reaction Scheme I:

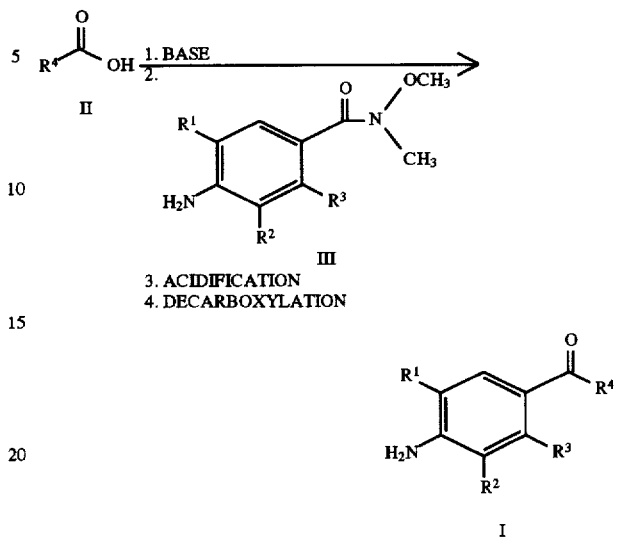

in which each $R^1$, $R^2$, $R^3$ and $R^4$ are as defined in the Summary of the Invention, with the reactions applying particularly well to the presently preferred embodiments.

The compounds of Formula I can be prepared by a process which comprises reacting a compound of Formula II, or a protected derivative thereof, with a compound of Formula III, acidifying, decarboxylating, and when necessary removing any protective groups. The reaction between the compounds of Formulae II and III is carried out in the presence of a strong base (e.g., lithium diisopropylamide) and in a suitable solvent (e.g., tetrahydrofuran (THF) and hexamethylphosphoric triamide (HMPA), preferably a 50/50 mixture of THF and HMPA) at −40° to 0° C. The reaction mixture is then acidified and extracted into an appropriate solvent (e.g., mesthylene chloride). The decarboxylation can then be carried by standard methods to form a compound of Formula I. The preparation of a compound of Formula I by the process depicted in Reaction Scheme I is described in Example 3.

Compounds of Formula II in which $R^4$ is a group of Formula (a) can be prepared by reacting a halo($C_{4-6}$) alkionate with a compound of the formula $NHR^5R^6$ to give an aminated ($C_{4-6}$)alkionate and then hydrolyzing and converting to the acid addition salt. The reaction with the compound of the formula $NHR^5R^6$ is carried out in a suitable solvent (e.g., 1-methyl-2-pyrrolidinone, DMF, etc.l at 25° to 50° C., preferably at approximately 35° C., and requires 12 to 48 hours. The hydrolysis can be effected with acid (e.g., hydrochloric acid, sulfuric acid, etc.) at 90° to 110° C., preferably at approximately 100° C., and requires 2 to 4 hours. The acid addition salt can be recovered by crystallization from the solvent (e.g., by diluting with acetone).

Compounds of Formula II in which $R^4$ is a group of Formula (b) may be prepared from an appropriately 1-substituted 4-hydroxypiperidine or 4-hydroxymethylpiperidine. The 4-piperidinealcohol is converted to the corresponding sulfonate (i.e., to 4-(p-toluenesulfonyloxy)piperidine or 4-[(p-toluenesulfonyloxy) methyl]piperidine) by reacting with p-toluenesulfonyl chloride. The sulfonate is then reacted with diethyl malonate in the presence of base to produce a 4-[di(ethoxycarbonyl) alkyl]piperidine. The 4-[di(ethoxycarbonyl)alkyl]piperidine is then converted to a dicarboxylic acid which upon decarboxylation gives a compound of Formula II.

Protected derivatives of compounds of Formula II are prepared from the protected derivative of the piperidinealcohols (e.g., 1-tert-butoxycarbonyl-4-piperidinemethanol). The preparation of a protected derivative of Formula II in which $R^4$ is Formula (b) is described in Example 1.

The compounds of Formula III can be prepared by reacting an appropriate 4-amino-5-halobenzoic acid with N,O-dimethylhydroxylamine hydrochloride. The reaction is carried out in the presence of carbonyldiimidazole in a suitable solvent (e.g., N,N-dimethylformamide (DMF)). The preparation of a compound of Formula III is described in Example 2.

Alternatively, compounds of Formula I in which $R^4$ is a group of Formula (b) and $R^7$ is not hydrogen can be prepared by alkylating a corresponding compound of Formula I in which $R^7$ is hydrogen with a compound of the formula L-$R^{20}$ in which L is a leaving group and $R^{20}$ is $(C_{1-8})$alkyl, $(C_{3-8})$alkenyl, phenyl$(C_{1-4})$alkyl (wherein the phenyl is substituted as defined in the Summary of the Invention) or —$(CH_2)_zR^{12}$ (wherein z and $R^{12}$ are as defined in the Summary of the Invention). The alkylation is carried out under standard amide alkylating conditions (Luh, T.; Fung S. H. *Synth. Commun.* 1979, 9, 757), in an inert solvent (e.g., acetonitrile, DMF, THF, etc.), and at a reaction temperature of 20° C. to 100° C. and requires 1 to 48 hours.

The alkylation can also be carried via a phase-transfer catalyst (PTC) system, i.e., with catalyst in a liquid-liquid two phase solvent system (Gajda, T.; Zwierzak, A. *Synthesis, Communications* 1981, 1005), or preferably a solid-liquid system (Yamawaki, J.; Ando, T.; Hanafusa, T. *Chem. Lett.* 1981, 1143; Koziara, A.; Zawaszki, S; Zwierzak, A. *Synthesis* 1979, 527, 549). A liquid—liquid two-phase system is comprised of an aqueous phase consisting of a concentrated alkali hydroxide solution (e.g., 50% aqueous sodium hydroxide), an organic phase comprised of an inert water-immiscible organic solvent, and an appropriate catalyst. A solid-liquid system consists of a powdered alkali hydroxide/ alkali carbonate suspended in an organic solvent and catalyst.

The reaction is effected by slowing adding the alkylating agent to a PTC system containing the compound of Formula I until the alkylating agent is 10 to 50% in excess. The reaction mixture is kept at reflux until the reaction is complete. The mixture is then cooled to room temperature and the product is isolated by conventional methods. Suitable organic solvents include benzene, toluene, and the like. Appropriate catalysts include alumina coated with potassium fluoride and quaternary ammonium sulfates such as tetra-n-butylammonium hydrogen sulfate and tricaprylylmethylammonium chloride. The alkylation of a compound of Formula I (b) in which $R^7$ is hydrogen is described in Example 10.

Compounds of Formula I in which $R^4$ is a group of Formula (b) and $R^7$ is —$(CH_2)_2NHC(O)R^{14}$, —$(CH_2)_2NHSO_2R^{14}$, —$(CH_2)_2NHSO_2NR^{14}R^{15}$ or —$(CH_2)_2NHC(O)NR^{14}R^{15}$ wherein $R^{14}$ and $R^{15}$ are as defined in the Summary of the Invention) can be prepared by alkylating a compound of Formula I in which $R^7$ is hydrogen with a compound of the formula X-$R^{21}$ in which X is azacycloprop-1-yl and $R^{21}$is —C(O)$R^9$, —$SO_2R^{14}$, —$SO_2NR^{14}R^{15}$ or —C(O)$NR^{14}R^{15}$. The alkylation is carried out in a suitable solvent (e.g., THF) at 0 to 20° C. The preparation of a compound of Formula I(b) in which $R^7$ is 2-[(methylsulfonyl)amino]ethyl is described in Example 11.

A method for making compounds of Formula I in which $R^2$ is hydrogen and $R^4$ is a group of Formula (a) is depicted by the following Reaction Scheme II:

REACTION SCHEME II

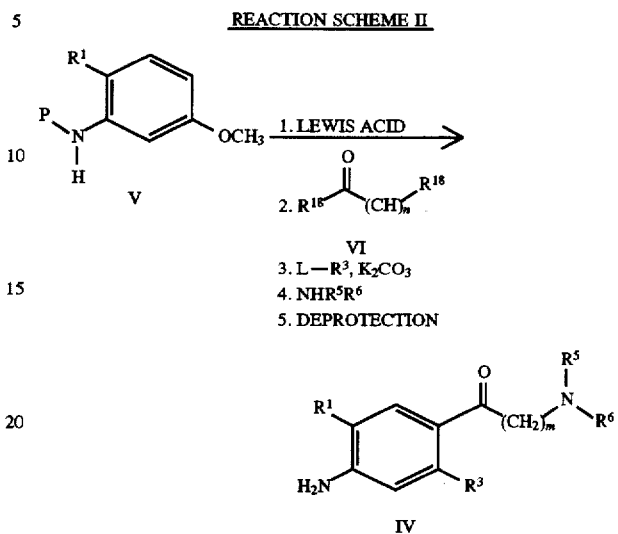

in which P is a protective group, $R^{18}$ is halo or hydroxy, $R^{19}$ is halo and L is a leaving group and each n, $R^1$, $R^3$, $R^5$ and $R^6$ are as defined in the Summary of the Invention.

The compounds of Formula I in which $R^2$ is hydrogen and $R^4$ is a group of Formula (a) (Formula IV) can be prepared by a process which comprises reacting a compound of Formula V with a compound of Formula VI; alkylating with a compound of the formula L-$R^3$; reacting with a compound the formula $HNR^5R^6$, or the N-oxide thereof; and removing the protective group.

The reaction between the compound of Formula V and the compound of Formula VI is carried out in the presence of a Lewis acid (e.g., aluminum chloride ($AlCl_3$), boron trifluoride, hydrogen fluoride, phosphosporic acid, etc., preferably $AlCl_3$) and in a suitable solvent (e.g., ethylene dichloride (EDC), methylene chloride, carbon disulfide, etc., preferably EDC) to form a 2-hydroxyphenylalkanone.

Alkylation of the 2-hydroxyphenylalkanone with the compound of the formula L-$R^3$ is carried out in the presence of potassium carbonate in a suitable solvent (e.g., methyl ethyl ketone (MEK), DMF, ethanol, THF, etc., preferably MEK) at 40 to 200° C. The reaction with the compound of the formula $HNR^5R^6$ is carried out in a suitable solvent (e.g., DMF, ethanol, THF, toluene, etc., preferably DMF) at 40 to 200° C. Deprotection can be carried out by any means that selectively removes the protective group. The preparation of a compound of Formula I(a) by the above process is described in Example 4.

The compounds of Formula VI are either available commercially (e.g., 5-chlorovaleric acid and 5-chlorovaleryl chloride) or can otherwise be readily prepared by halogenation of the corresponding alkanoic acid. The N-acetyl-halo-5-methoxyanilines of Formula V are either commercially available or can otherwise be obtained from N-acetyl-3-methoxyaniline. For example, a compound of Formula V in which $R^1$ is bromide can be prepared by reacting N-acetyl-3-methoxyaniline with bromine in a suitable solvent (e.g., dichloroethane).

The compounds of the formula $HNR^{56}$ (e.g., amines such as dimethylamine, diethylamine, diprop-1-ylamine, etc., and azacycloalkanes such as pyrrolidine, piperidine, pyrrolidine, morpholine, 4-phenylpiperidine, 4-methylpipesridine, etc.)

are known and available commercially or otherwise can be synthesized by methods known to those of ordinary skill in the art.

In variations upon Reaction Scheme II, compounds of Formula I may be prepared by reacting, in the presence of a Lewis acid, a compound of Formula V with a compound of Formula VI; reacting with a compound of the formula HNR$^5$R$^6$, or the N-oxide thereof; alkylating with a compound of the formula L-R$^3$; and removing the protective group; or by reacting a compound of Formula VI with a compound of the formula HNR$^5$R$^6$, or the N-oxide thereof; reacting, in the presence of a Lewis acid, with a compound of Formula V; alkylating with a compound of the formula L-R$^3$; and removing the protective group.

A method for making compounds of Formula I in which R$^4$ is a group of Formula (b) wherein q is 2 and R$^7$ is hydrogen is depicted by the following Reaction Scheme III:

REACTION SCHEME III

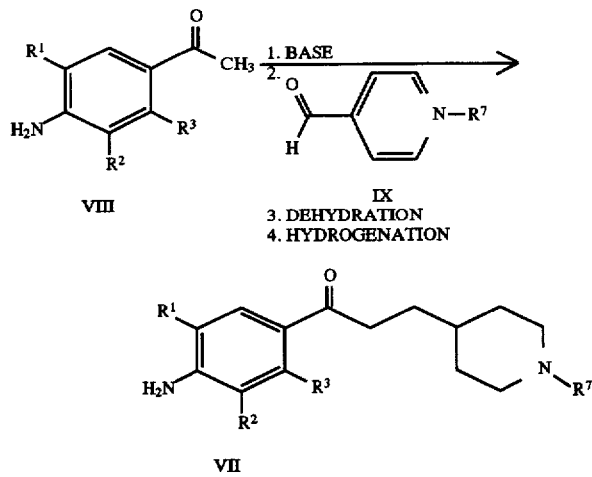

in which R$^1$, R$^2$, R$^3$ and R$^7$ are as defined in the Summary of the Invention.

Compounds of Formula I in which R$^4$ is a group of Formula (b) wherein p is 0, q is 2 and R$^7$ is hydrogen can be prepared by a process which comprises reacting a compound of Formula VIII with a compound of Formula IX to give a 3-pyridin-4-yl-3-hydroxy-propan-1-one derivative, dehydrating the 3-hydroxypropan-1-one to give a 3-pyridin-4-ylpropen-1-one derivative, and then hydrogenating to give the corresponding 3-piperidin-4-yl-propan-1-one. The reaction between the compounds of Formulae VIII and IX is carried out in the presence of a strong base (e.g., lithium diisopropylamide) in a suitable solvent (e.g., THF) at –50° to 50° C. Dehydration of the 3-hydroxypropan-1-one is carried out by standard methods (e.g., acid-catalyzed dehydration). If the reaction between the compound of Formulae VIII and IX is carried out in the presence of potassium hydroxide, the dehydration occurs spontaneously and the reaction proceeds to the 3-pyridin-4-yl-2-propen-1-one in a single step.

Hydrogenation of the 3-pyridin-4-yl-2-propen-1-one is carried out by with an appropriate catalyst (e.g., 5% rhodium-alumina, 10% palladium on carbon, platinum dioxide, palladium dihydroxide, etc.) in a suitable solvent (e.g., acetic acid, ethanol, DMF, THF, etc.) at 5 to 60 psi and requires 1 to 48 hours. The preparation of a compound of Formula I(b) by the process characterized above is described in Example 7.

Alternatively, hydrogenation of the 3-pyridin-4-yl-2-propen-1-one is carried out by (i) hydrogenating the 2-propen-1-one until conversion to the corresponding 3-pyridin-4-ylpropan-1-one is complete, (ii) optionally alkylating the propan-1-one with a compound of the formula L-R$^{20}$ or X-R$^{21}$ (wherein R$^{20}$ and R$^{21}$ are as defined above), and then (iii) continuing hydrogenation to give the corresponding 3-piperidin-4-ylpropan-1-one. Hydrogenation of the propenone to the 3-pyridin-4-ylpropan-1-one is carried out with an appropriate catalyst (5% palladium on carbon, 20% palladium hydroxide, etc.) in a suitable solvent (e.g., THF, acetic acid, DMF, ethanol, etc.) at 5 to 60 psi and requires 1 to 48 hours. The preparation of a compound of Formula I(b) in which R$^7$ is 3-(4-methoxyphenyl)prop-1-yl is described in Example 13.

The optional reaction with the compound of the formula L-R$^{20}$ or X-R$^{21}$ is carried out as described above for the alkylation of compounds of Formula I in which R$^4$ is a group of Formula (b) and R$^7$ is hydrogen. Hydrogenation of the 3-pyridin-4-yl-propan-1-one is carried out by with an appropriate catalyst (e.g., 5% rhodium-alumina, 10% palladium on carbon, platinum dioxide, palladium dihydroxide, etc.) in a suitable solvent (e.g., acetic acid, ethanol, DMF, THF, etc.) at 5 to 60 psi and requires 1 to 48 hours.

The compounds of Formula VIII can be prepared by methylation of the corresponding N-methoxy-N-methylbenzamide. The methylation is carried out by reacting the N-methoxy-N-methylbenzamide with methylating agent (e.g., methyllithium, methyl magnesium bromide, etc.) in a suitable solvent (e.g., THF, ether, etc.) at –20° to 20° C. and requires 1 to 24 hours. The preparation of a compound of Formula VIII in which R$^1$ is chloro and R$^3$ is methoxy is described in Example 5.

Alternatively, compounds of Formula VIII in which R$^2$ and R$^3$ together are ethylenedioxy can be prepared by halogenating a protected derivative of 4'-amino-2',3'-ethylenedioxyacetophenone and then deprotecting. The halogenation can be carried out by reacting the acetophenone with a halogenating agent (e.g., N-chlorosuccinimide, chlorine, etc.) in a suitable solvent (e.g., DMF, acetonitrile, etc.) at –20° to 80° C. and requires 1 to 24 hours. Deprotection can be carried out with base (e.g., sodium hydroxide and the like) in a suitable solvent (e.g., methanol and the like).

The 4'-amino-2',3'-ethylenedioxyacetophenone can be prepared by reacting 5',6'-dichloro-2',3'-ethylenedioxyacetophenone with fuming nitric acid to give 5',6'-dichloro-2',3'-ethylenedioxy-4'-nitroacetophenone and then reducing. The reaction with the nitric acid is carried out at 0° to 25° C. and requires 0.5 to 2 hours. The reduction is carried out in the presence of catalyst (e.g., 10% palladium on carbon) in a suitable solvent (e.g., ethanol, acetic acid, ethyl acetate, etc.) at room temperature and requires 1 to 24 hours. Protection of the 4'-amino-2',3'-ethylenedioxyacetophenone can be effected by reacting with a suitable protecting agent. For example, 2',3'-ethylenedioxy-4'-(methylcarbonylamino)acetophenone is prepared by reacting the unprotected acetophenone with acetic anhydride in pyridine. The reaction with the acetic anhydride is carried out at 0 to 30° C. and requires 1 to 8 hours.

The 5',6'-dichloro-2',3'-ethylenedioxy-4'-nitroacetophenone can be prepared by chlorinating 1,4-benzodioxane to give 6,7-dichloro-1,4-benzodioxane and then acetylating. The chlorination can be carried out by treating the benzodioxane with chlorine gas in acetic acid at 0 to 20° C. and requires 1 to 8 hours. The acetylation can be effected by reacting the 6,7-dichloro-1,4-benzodioxane with acetyl chloride in the presence of a Lewis acid in a suitable solvent (e.g., 1,2-dichloroethane, carbon disulfide, nitrobenzene, etc.) at 20 to 40° C. and requires 24 to 48 hours.

A method for making compounds of Formula I in which $R^4$ is a group of Formula (a) is depicted by the following Reaction Scheme IV:

REACTION SCHEME IV

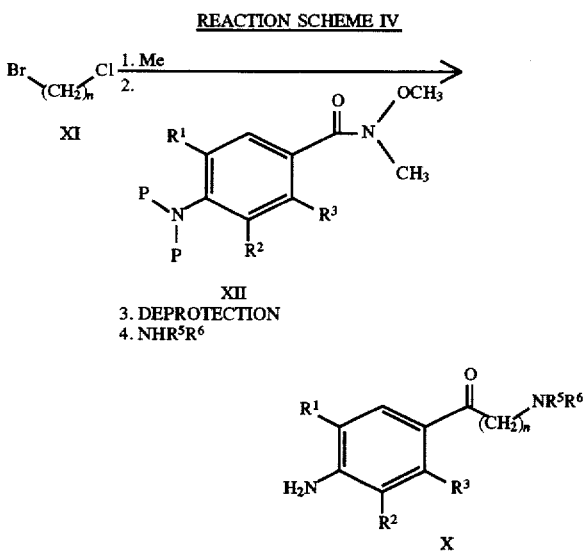

XII
3. DEPROTECTION
4. $NHR^5R^6$ in which each P is a protective group and $R^1$, $R^2$, $R^3$, $R^5$ and $R^6$ are as defined in the Summary of the Invention.

Compounds of Formula I in which $R^4$ is a group of Formula (a) can be prepared by a process which comprises treating a compound of Formula XI with magnesium to give a Grignard reagent, reacting the Grignard reagent with a compound of Formula XII to give the corresponding protected ($C_{4-6}$)alkanone, deprotecting and then reacting the unprotected alkanone with a compound of the formula $NHR^5R^6$.

The treatment with the magnesium is carried out by adding the compound of Formula XI under nitrogen to a suspension of magnesium in a suitable solvent (e.g., THF, diethyl ether, etc.) at a rate such that the liberation of heat is controlled and then allowing the reaction to proceed at 20° to 25° C. for 1 to 2 hours. The reaction with the Grignard reagent is carried out by cooling a solution of the compound of Formula XII in a suitable solvent (e.g., THF, diethyl ether, etc.) to between −10° and −20° C., preferably to approximately −15° C. and then adding the suspension containing the Grignard reagent, cooled to approximately the same temperature, and allowing the reaction to proceed at 0° to 15° C., preferably at approximately 10° C., for 1 to 2 hours.

Deprotection can be effected by any means which removes the protective group and gives the desired unprotected alkanone in good yield. The reaction with the unprotected alkanone is carried out under nitrogen with 3 to 6 equivalents, preferably 3 to 4 equivalents, of $NHR^5R^6$ in a suitable solvent (e.g., DMF, NMP, etc.) at 55° to 85° C., preferably at 55 to 60° C., and requires 4 to 8 hours. The preparation of a compound of Formula I by the process characterized above is described in Example 14.

Compounds of Formula XII can be prepared by reacting a compound of Formula III with a suitable protecting agent. A detailed description of the techniques applicable to protective groups and their removal can be found in T. W. Greene, Protective Groups in Organic Synthesis, John Wiley & Sons, Inc. 1981. For example, compounds of Formula XII in which the protective groups are trimethylsilyl can be prepared by reacting a compound of Formula III with chlorotrimethylsilane. The reaction is carried out in the presence of strong base (e.g., tert-butylmagnesium chloride, lithium bis(trimethylsilyl)amide (LiHMDS), etc.) under nitrogen in a suitable solvent (e.g., THF, ether, etc.) at −15° to 15° C., preferably at approximately 10° C., and requires 15 to 30 minutes. Deprotection of a compound of Formula XII in which the protective groups are trimethylsilyl can be effected with acid (e.g., hydrochloric acid, trifluoroacetic acid, etc.).

A method for making compounds of Formula I in which $R^4$ is a group of Formula (a) is depicted by the following Reaction Scheme V:

REACTION SCHEME V

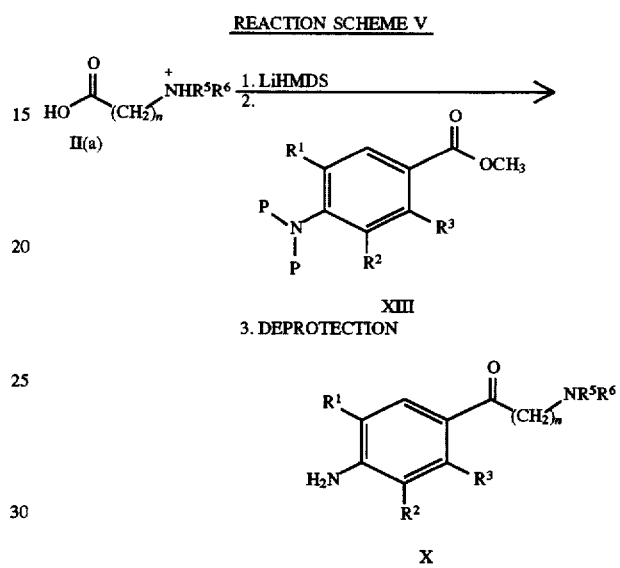

in which each P is a protective group and $R^1$, $R^2$, $R^3$, $R^5$ and $R^6$ are as defined in the Summary of the Invention.

Compounds of Formula I in which $R^4$ is a group of Formula (a) can be prepared by reacting the acid addition salt of a corresponding compound of Formula II (Formula II(a)) with a compound of Formula XIII in the presence of a strong base (e.g., LiHMDS, sodium bis(trimethylsilyl) amide, lithium duisopropylamide, preferably LiHMDS) and then deprotecting. The reaction between the compounds of Formulae II (a) and XIV can be carried out by cooling a mixture containing the compound of Formula II(a) in a suitable solvent (e.g., THF, ethylene glycol dimethyl ether, diethyl ether, etc.) to between 10° and 30° C., preferably to approximately 15° C.; adding a minimum of 3 equivalents of the strong base and allowing 0.5 to 2 hours at 10° to 30° C., preferably at approximately 20° C.; cooling the mixture to between 0° and 10° C., preferably to approximately 50° C.; and then adding the compound of Formula XIII and allowing the reaction to proceed at 40° to 55° C. for approximately 4 hours. Deprotection can be effected by any means which removes the protective group and gives the desired unprotected product in good yield. A suitable protective group for the compound of Formula XIII is trimethylsilyl which can be readily removed with acid. The preparation of a compound of Formula I by the process characterized above is described in Example 15.

Compounds of Formula XIII can be prepared by reacting a corresponding benzoic acid with methanol in the presence of thionyl chloride and then adding the protective groups. The reaction with the benzoic acid is carried out at 0° to 25° C., preferably at approximately 15° C., and requires 1 to 4 hours. The protection can be carried out with chlorotrimethylsilane in the presence of strong base (e.g., tert-butylmagnesium chloride, LiHMDS, etc.) in a suitable solvent.

Additional Processes:

Compounds of Formula I in which $R^3$ is $(C_{2-4})$alkyloxy or phenyl $(C_{1-4})$alkyloxy can be prepared by demethylating a compound of Formula I in which $R^3$ is methoxy, and then alkylating with a compound of the formula L-$R^{22}$ in which $R^{22}$ is $(C_{2-4})$alkyl or phenyl $(C_{1-4})$alkyl (wherein the phenyl is optionally substituted with one to three substituents independently selected from halo, hydroxy, $(C_{1-4})$alkyl, $(C_{1-4})$alkyloxy, amino, aminocarbonyl, $(C_{1-4})$alkylamino, di$(C_{1-4})$alkylamino, $(C_{1-4})$alkanoylamino and 3,4-methylenedioxy). The demethylation is carried out by standard methods with an appropriate demethylating agent (e.g., boron tribromide, boron trichloride, etc.) and in an aprotic solvent (e.g., methylene chloride, dichloroethane, etc.) or with acid (e.g., aqueous hydrobromic acid) to form the corresponding 2-hydroxyphenylalkan-1-one. The alkylation is carried out in the presence of potassium carbonate in a suitable solvent (e.g., methyl ethyl ketone (MEK), DMF, ethanol, THF, etc., preferably MEK) at 40° to 200° C. The preparation of a compound of Formula I by the above process is described in Example 12.

The compounds of Formula I wherein p is 1 (compounds of Formula I in the N-oxide form) can be prepared by oxidizing a compound of Formula I in which p is 0. The oxidation is carried out at a reaction temperature of approximately 0° C. with an appropriate oxidizing agent and in a suitable inert, organic solvent. Suitable oxidizing agents include hydrogen peroxide or peroxy acids such as trifluoroperacetic acid, permaleic acid, perbenzoic acid, peracetic acid, and m-chloroperoxybenzoic acid. Suitable solvents include halogenated hydrocarbons, e.g., methylene chloride, and alcohols. Alternatively, the compounds of Formula I wherein p is 1 may be prepared using N-oxide derivatives of the starting materials or intermediates.

Compounds of Formula I in which p is 0 can be prepared by reducing a compound of Formula I wherein p is 1. The reduction is carried out under standard conditions with an appropriate reducing agent in a suitable solvent. The mixture is occasionally agitated while the reaction temperature is gradually increased over a range of 0° C. to 80° C. Appropriate reducing agents include sulfur, sulfur dioxide, triarylphosphines (e.g., triphenylphosphine), alkali borohydrides (e.g., lithium borohydride, sodium borohydride, etc.), phosphorus trichloride and tribromide. Suitable solvents include acetonitrile, ethanol or aqueous dioxane.

Compounds of Formula I may be prepared as pharmaceutically acceptable acid addition salts by reacting the free base forms of a compound of Formula I with a pharmaceutically acceptable inorganic or organic acid. Alternatively, the pharmaceutically acceptable base addition salts of compounds of Formula I may be prepared by reacting the free acid forms of compounds of Formula I with pharmaceutically acceptable inorganic or organic bases. Inorganic and organic acids and bases suitable for the preparation of the pharmaceutically acceptable salts of compounds of Formula I are set forth in the definitions section of this application. Alternatively, the salt forms of the compounds of Formula I may be prepared using salts of the starting materials or intermediates.

The free acid or free base forms of the compounds of Formula I can be prepared from the corresponding base addition salt or acid addition salt form. For example, compounds of Formula I in an acid addition salt form may be converted to the corresponding free base by treating with a suitable base (e.g., ammonium hydroxide solution, sodium hydroxide, etc.). Compounds of Formula I in a base addition salt form may be converted to the corresponding free acid by treating with a suitable acid (e.g., hydrochloric acid, etc).

In summary, the processes for preparing the compounds of this invention are:

(A) for the preparation of a compound of Formula I, reacting, in the presence of a strong base, a compound of Formula II:

or the protected derivative thereof, in which $R^4$ is as defined in the Summary of the Invention; with a compound of Formula III:

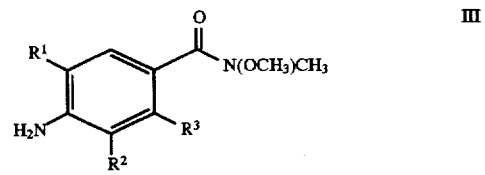

in which each $R^1$, $R^2$ and $R^3$ are as defined in the Summary of the Invention; acidifying; decarboxylating; and when necessary removing any protective groups; or (B) for the preparation of a compound of Formula I in which $R^2$ is hydrogen and $R^4$ is a group of Formula (a), reacting, in the presence of a Lewis acid, a compound of Formula V:

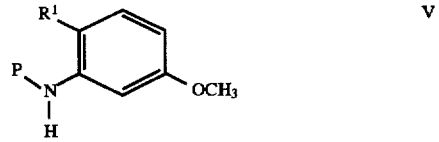

in which P is a protective group and $R^1$ is halo, with a compound of Formula VI:

in which $R^{18}$ is halo or hydroxy and $R^{19}$ is halo and n is 3, 4 or 5; alkylating with a compound of the formula L-$R^3$ in which L is a leaving group and $R^3$ is as defined above; reacting with a compound the formula HN$R^5R^6$, or the N-oxide thereof, in which $R^5$ and $R^6$ are as defined above; and deprotecting; or (C) for the preparation of a compound of Formula I in which $R^4$ is a group of Formula (b) wherein p is 0 and q is 2, reacting a compound of Formula VIII:

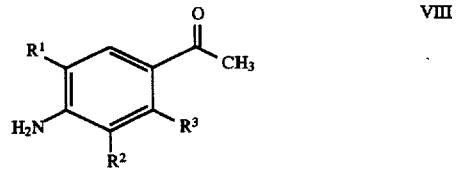

in which $R^1$, $R^2$ and $R^3$ are as defined in the Summary of the Invention; with a compound of Formula IX:

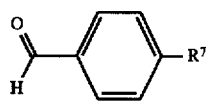

IX in which $R^7$ is as defined in the Summary of the Invention; dehydrating; and then hydrogenating; or (D) for the preparation of a compound of Formula I in which $R^4$ is a group of Formula (a), treating a compound of Formula XI:

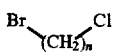

XI in which n is as defined in the Summary of the Invention, with magnesium to give a corresponding Grignard reagent, reacting the Grignard reagent with a compound of Formula XII:

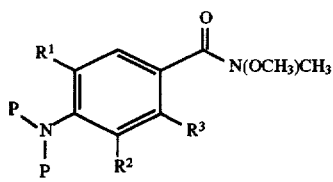

XII in which each P is a protective group and $R^1$, $R^2$ and $R^3$ are as defined in the Summary of the Invention, deprotecting and then reacting with a compound of the formula $NHR^5R^6$; or (E) for the preparation of a compound of Formula I in which $R^4$ is a group of Formula (a), reacting, in the presence of a strong base, a compound of Formula II(a):

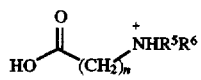

II(a)

in which $R^5$ and $R^6$ is as defined in the Summary of the Invention, with a compound of Formula XIII:

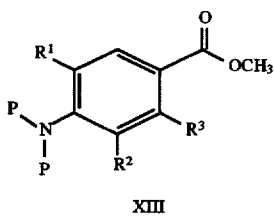

XIII in which each P is a protective group and $R^1$, $R^2$ and $R^3$ are as defined in the Summary of the Invention; or (F) optionally alkylating a compound of Formula I in which $R^4$ is a group of Formula (b) and $R^7$ is hydrogen with a compound of the formula $L-R^{20}$ in which L is leaving group and $R^{20}$ is $(C_{1-8})$alkyl, $(C_{3-8})$alkenyl, phenyl$(C_{1-4})$alkyl (wherein the phenyl is optionally substituted with one to three substituents independently selected from $(C_{1-4})$alkyloxy, methylenedioxy, ethylenedioxy or halo) or $L-(CH_2)_zR^{12}$ (wherein z and $R^{12}$ are as defined in the Summary of the Invention) to give a compound of Formula I in which $R^4$ is a group of Formula (b) wherein $R^7$ is not hydrogen; or (G) optionally alkylating a compound of Formula I in which $R^4$ is a group of Formula (b) and $R^7$ is hydrogen with a compound of the formula $X-R^{21}$ in which X is azacycloprop-1-yl and $R^{21}$ is $—C(O)R^4$, $—SO_2R^{14}$, $—SO_2NR^{14}R^{15}$ or $—CONR^{14}R^{15}$ (wherein $R^{14}$ and $R^{15}$ are as defined in the Summary of the Invention) to give a compound of Formula I in which $R^4$ is a group of Formula (b) wherein $R^7$ is $—CH_2CH_2NHC(O)$ $R^4$, $—CH_2CH_2NHSO_2R^{14}$, $—CH_2CH_2NHSO_2NR^{14}R^5$ or $—CH_2CH_2NHCONR^{14}R^{15}$; or (H) optionally demethylating a compound of Formula I in which $R^3$ is methoxy, and then alkylating with a compound of the formula $L-R^{22}$ in which $R^{22}$ is $(C_{2-4})$alkyl or phenyl$(C_{1-4})$alkyl (wherein the phenyl is optionally substituted with one to three substituents independently selected from halo, hydroxy, $(C_{1-4})$alkyl, $(C_{1-4})$alkyloxy, nitro, amino, aminocarbonyl, $(C_{1-4})$alkylamino, di$(C_{1-4})$alkylamino, $(C_{1-4})$alkanoylamino and 3,4-methylenedioxy) to give a compound of Formula I in which $R^3$ is $(C_{2-4})$alkyloxy or phenyl $(C_{1-4})$alkyloxy (wherein the phenyl is optionally substituted as defined in the Summary of the Invention); or (I) optionally oxidizing a compound of Formula I in which p is 0 to give a compound of Formula I in which p is 1; or (J) optionally reducing a compound of Formula I in which p is 1 to give a compound of Formula I in which p is 0; or (K) optionally reacting the corresponding non-salt form of a compound of Formula I with a pharmaceutically acceptable inorganic or organic acid or base to give a pharmaceutically acceptable salt; or (L) optionally reacting the corresponding acid addition salt or base addition salt form of a compound of Formula I with a suitable base or acid, respectively, to give the free acid or free base.

In any of the above last step processes, a reference to Formulae I, II, II(a), III, IV, V, VI, VII, VIII, IX, X, XI, XII and XIII refers to such formulae wherein $R^1$, $R^2$, $R^3$, $R^4$, $R^5$ and $R^7$ are as defined in their broadest definitions set forth in the Summary of the Invention, with the processes applying particularly well to the presently preferred embodiments.

EXAMPLES:

Example 1

3-[1-(tert-Butoxycarbonyl)piperidin-4-yl]propionic acid

The following is the preparation of a protected derivative of a compound of Formula II in which $R^4$ is a group of Formula (b) wherein q is 2.

Step (a)

4-Hydroxymethylpiperidine (27.0 g, 262 mmol) and di-tert-butyldicarbonate (51.2 g, 235 mmol) were dissolved in THF (300 mL) and the solution was stirred 12 hours at room temperature. The mixture was concentrated in vacuo and the residue was dissolved in ether. The ether solution was washed with water and then with brine, and dried over sodium sulfate. Evaporation of the solvents gave a residue (51.0 g) as an oil.

The oil residue was dissolved in pyridine (200 mL) and the solution was cooled to 0° C. p-Toluenesulfonyl chloride (47.5 g, 250 mmol) was then added to the solution and the mixture was stored at 5° C. for 12 hours. The mixture was poured into water and extracted into ethyl acetate. The ethyl acetate extract was washed with 5% HCl, with water, and then with brine. The ethyl acetate was then dried over sodium sulfate and then evaporated. Crystallization from ethyl acetate-hexane gave 1-(tert-butoxycarbonyl)-4-[(p-toluenesulfonyloxy)methyl]-piperidine (50 g, 136 mmol), m.p. 71°–72° C.

Step (b)

Diethyl malonate (10.4 g, 65 mmol) was added to a solution of sodium ethoxide (4.42 g, 65 mmol) in ethanol (75 mL). 1-(tert-Butoxycarbonyl)-4-[(p-toluenesulfonyloxy) methyl]piperidine (25 g, 68 mmol), prepared as in Example 1, Step (a), was added and the mixture was heated at reflux for 4 hours. The mixture was cooled and partitioned between ethyl acetate and water. The ethyl acetate layer was separated, washed with water and then brine, dried over sodium sulfate, and evaporated. Purification of the residue by silica gel chromatography (25% ethyl acetate-hexane) gave 1-(tert-butoxycarbonyl)-4-[2,2-di(ethoxycarbonyl) ethyl]piperidine (16 g, 45 mmol) as an oil.

Step (c)

1-(tert-Butoxycarbonyl)-4-[2,2-di(ethoxycarbonyl)ethyl] piperidine (12.2 g, 34 mmol), prepared as in Example 1, Step (b), and potassium hydroxide (4.2 g, 75 mmol) were combined in ethanol (10 mL), THF (20 mL), and water (50 mL) and the mixture was heated at reflux for 3 hours. The mixture was cooled and washed with ether, acidified with sulfuric acid, and extracted into ether. The ether was dried over sodium sulfate and evaporated. Crystallization of the residue from ether gave 1-(tert-butoxycarbonyl)-4-[2,2-di(carboxy) ethyl]piperidine (8.5 g, 28 mmol) which was heated in an oil bath to 165° C. until evolution of $CO_2$ ceased (approximately 10 minutes). The residue was cooled and upon crystallization gave 3-[1-(tert-butoxycarbonyl) piperidin-4-yl]propionic acid (7.2 g, 28 mmol), m.p. 81°–83° C.

Example 2

N-Methoxy-N-methyl-4-amino-5-chloro-2-methoxybenzamide

The following is the preparation of a compound of Formula III in which $R^1$ is chloro and $R^3$ is methoxy.

4-Amino-5-chloro-2-methoxybenzoic acid (10.1 g, 50 mmol) was dissolved in DMF (50 mL). Carbonyldiimidazole (8.9 g, 55 mmol) was added to the solution and the mixture was stirred for 15 minutes. Triethylamine (7 mL, 5.1 g, 50 mmol) and N,O-dimethylhydroxylamine hydrochloride (6.3 g, 65 mmol) were added and the mixture was stirred for 12 hours. The mixture was then diluted with water and extracted into ethyl acetate. The ethyl acetate extract was washed with 5% HCl, with water, and then with brine. The extract was dried over sodium sulfate and then evaporated. Crystallization from ethyl acetate gave N-methoxy-N-methyl-4-amino-5-chloro-2-methoxybenzamide (10 g, 41 mmol), m.p. 134°–135° C.

Example 3

1-(4-Amino-5-chloro-2-methoxyphenyl)-3-(1-piperidin-4-yl)propan-1-one

The following is the preparation of a compound of Formula I in which $R^1$ is chloro, $R^3$ is methoxy, $R^4$ is a group of Formula (b) in which p is 0, q is 2, and $R^7$ is hydrogen.

Step (a)

3-[1-(tert-Butoxycarbonyl)piperidin-4-yl]propionic acid (4.6 g, 18 mmol), prepared as in Example 1, was dissolved in HMPA (10 mL) and THF (10 mL), and this solution was added to a −20° solution of lithium diisopropylamide (60 mmol). The mixture was warmed to 0° C., stirred for 30 minutes, and then cooled to −40° C. N-Methoxy-N-methyl-4-amino-5-chloro-2-methoxybenzamide (4.9 g, 20 mmol), prepared as in Example 2, was dissolved in HMPA (10 mL) and THF (10 mL) and this solution was added to the mixture. The mixture was allowed to warm to 0° C. over 1 hour, then diluted with water, washed with ether, acidified with hydrochloric acid, and extracted into methylene chloride. The methylene chloride extract was concentrated in vacuo and the residue was heated in an oil bath to 140° C. for 30 minutes. The mixture was cooled, partitioned between water and ethyl acetate. The ethyl acetate layer was separated, washed with 5% sodium hydroxide and then brine, dried over sodium sulfate, and evaporated. Purification by silica gel chromatography (40% ethyl acetate-hexane) gave 1-(4-amino-5-chloro-2-methoxyphenyl)-3-[1-(tert-butoxycarbonyl)piperidin-4-yl]-propan-1-one (1.5 g, 3.8 mmol), m.p. 133°–134° C.

Step (b)

1-(4-Amino-5-chloro-2-methoxyphenyl)-3-[1-(tert-butoxycarbonyl)-piperidin-4-yl]propan-1-one (1.5 g, 3.8 mmol) was dissolved in methylene chloride (20 mL) and trifluoroacetic acid (5 mL) was added to the solution. After 30 minutes the solution was washed with aqueous ammonium hydroxide, and dried over sodium sulfate. Evaporation of the solvents gave 1-(4-amino-5-chloro-2-methoxyphenyl) -3-(piperidin-4-yl)-propan-1-one (1.1 g, 3.8 mmol), m.p. 138°–140° C.

Example 4

1-(4-Amino-5-chloro-2-methoxyphenyl)-5-(piperidin-1-yl)pentan-1-one

The following is the preparation of a compound of Formula I in which $R^1$ is chloro, $R^3$ is methoxy, and $R^4$ is a group of the Formula (a) wherein n is 4, p is 0, and $R^5$ and $R^6$ together are piperidin-1-yl.

Step (a)

N-Acetyl-2-chloro-5-methoxyaniline (10.0 g, 50 mmol), aluminum chloride (13.3 g, 100 mmol), and 5-chloropentanoyl chloride (11.7 g, 75 mmol) were combined in ethylene dichloride (100 mL) and the mixture was stirred at room temperature and under nitrogen for 7 days. The mixture was then poured onto crushed ice and extracted into methylene chloride. The methylene chloride extract was washed with water and then dried. The solvent was evaporated in vacuo. Crystallization of the residue from ethyl acetate/hexane gave 1-(4-acetylamino-5-chloro-2-hydroxyphenyl)-5-chloropentan-1-one (10.18 g, 35.1 mmol), m.p. 126°–128° C.

Proceeding as in Example 4, Step (a), but replacing 1,5-dichloro-pentan-1-one with 4-chlorobutyryl chloride, gave 1-(4-acetylamino-5-chloro-2-hydroxyphenyl)-4-chlorobutan-1-one, m.p. 103°–106° C.

Proceeding as in Example 4, Step (a), but replacing 1,5-dichlcoro-pentan-1-one with 1,5-dibromopentan-1-one and N-acetyl-2-chloro-5-methoxyaniline with N-acetyl-2-bromo-5-methoxyaniline, gave 1-(4-acetylamino-5-bromo-2-hydroxyphenyl)-5-bromopentan-1-one.

Step (b)

1-(4-Acetylamino-5-chloro-2-hydroxyphenyl)-5-chloropentan-1-one (1.07 g, 3.5 mmol), potassium carbonate (1.38 g, 10.0 mmol) and iodomethane (0.62 mL, 10.0 mmol) were combined in methyl ethyl ketone (20 mL) and stirred at reflux temperature for 4 hours, 15 minutes. The mixture was partitioned between ethyl acetate and water. The ethyl acetate layer was separated, washed in brine, dried over sodium sulfate, and then evaporated to leave a solid residue.

Crystallization of the residue from ethyl acetate-hexanes gave 1-(4-acetylamino-5-chloro-2-methoxyphenyl)-5-chloro-pentan-1-one (0.720 g, 2.37 mmol), m.p. 98°–100° C.

Proceeding as in Example 4, Step (b), but replacing 1-(4-acetylamino-5-chloro-2-hydroxyphenyl)-5-chloropentan-1-one with 1-(4-acetylamino-5-chloro-2-hydroxyphenyl)-4-chlorobutan-1-one, gave 1-(4-acetylamino-5-chloro-2-methoxyphenyl)-4-chlorobutan-1-one as an oil.

Proceeding as in Example 4, Step (b), but replacing iodomethane with 4-methoxybenzylchloride, gave 1-[4-acetylamino-5-chloro-2-(4-methoxybenzyloxy)-phenyl]-5-chloropentan-1-one, m.p. 147°–149° C.

Proceeding as in Example 4, Step (b), but replacing iodomethane with 3,4-dimethoxybenzylchloride, gave 1-[4-acetylamino-5-chloro-2-(3,4-dimethoxy-benzyloxy)phenyl]-5-chloropentan-1-one, m.p. 147° C.

Proceeding as in Example 4, Step (b), but replacing iodomethane with 3,5-dimethoxybenzylchloride, gave 1-(4-acetylamino-5-chloro-2-(3,5-dimethoxy-benzyloxy)phenyl]-5-chloropentan-1-one, m.p. 135°–137° C.

Proceeding as in Example 4, Step (b), but replacing iodomethane with 3,5-dimethoxybenzylchloride and 1-(4-acetylamino-5-chloro-2-hydroxyphenyl)-5-chloropentan-1-one with 1-(4-acetylamino-5-bromo-2-hydroxyphenyl)-5-bromo-pentan-1-one, gave 1-[4-acetylamino-5-bromo-2-(3,5-dimethoxybenzyloxy)phenyl]-5-bromopentan-1-one.

Proceeding as in Example 4, Step (b), but replacing iodomethane with 3,4-methylenedioxybenzylchloride, gave 1-[4-acetylamino-5-chloro-2-(3,4-methylenedioxybenzyloxy)phenyl]-5-chloropentan-1-one, m.p. 132°–134° C.

Proceeding as in Example 4, Step (b), but replacing iodomethanse with 2-(4-methoxyphenyl)-1-iodoethane, gave 1-{4-acetylamino-5-chloro-2-[2-(4-methoxyphen)ethoxy]phenyl}-5-chloropentan-1-one, m.p. 108°–110° C.

Proceeding as in Example 4, Step (b), but replacing iodomethane with 2-(3,4-dimethoxyphenyl)-1-iodoethane, gave 1-{4-acetylamino-5-chloro-2-[2-(3,4-dimethoxyphen)ethoxy]phenyl}-5-chloropentan-1-one.

Step (c)

1-(4-Acetylamino-5-chloro-2-methoxyphenyl)-5-chloropentan-1-one (0.72 g, 2.26 mmol), sodium iodide (0.15 g, 0.1 mmol), and piperidine (1.72 g, 20 mmol) were combined in DMF (8.0 mL) and the mixture was heated to 80° C. for 4.5 hours. Water was then added to form a precipitate. Filtration gave 1-(4-acetylamino-5-chloro-2-methoxyphenyl)-5-(piperidin-1-yl)pentan-1-one (0.8 g, 2.18 mmol), m.p. 74°–75° C.

1-(4-Acetylamino-5-chloro-2-methoxyphenyl)-5-(piperidin-1-yl)pentan-1-one was dissolved in 2N hydrochloric acid (25 mL) and the solution was stirred for 30 minutes. The solution was cooled in an ice bath to form a precipitate. The precipitate was collected by filtration and washed with water. Drying in a vacuum oven at 70° C. gave 1-(4-amino-5-chloro-2-methoxyphenyl)-5-(piperidin-1-yl)pentan-1-one hydrochloride (0.65 g, 2 mmol), m.p. 220°–221° C.

Proceeding as in Example 4, Step (c), but replacing 1-(4-acetylamino-5-chloro-2-methoxyphenyl)-5-chloropentan-1-one with 1-(4-acetylamino-5-chloro-2-methoxyphenyl)-4-chlorobutan-1-one and piperidine with diethylamine, gave 1-(4-amino-5-chloro-2-methoxy m.p. 145°–150° C.

Proceeding as in Example 4, Step (c), but replacing 1-(4-acetylamino-5-chloro-2-methoxyphenyl)-5-chloropentan-1-one with 1-(4-acetylamino-5-chloro-2-methoxyphenyl)-4-chlorobutan-1-one and piperidine with pyrrolidine, gave 1-(4-amino-5-chloro-2-methoxyphenyl)-4-(pyrrolidin-1-yl)butan-1-one hydrochloride, m.p. 221°–224° C.

Proceeding as in Example 4, Step (c), but replacing 1-(4-acetylamino-5-chloro-2-methoxyphenyl)-5-chloropentan-1-one with 1-(4-acetylamino-5-chloro-2-methoxyphenyl)-4-chlorobutan-1-one, gave 1-(4-amino-5-chloro-2-methoxy-phenyl)-4-(piperidin-1-yl)butan-1-one hydrochloride, m.p. 235°–238° C.

Proceeding as in Example 4, Step (c), but replacing piperidine with dimethylamine, gave 1-(4-amino-5-chloro-2-methoxyphenyl)-5-dimethylamino-pentan-1-one hydrochloride, m.p. 219°–220° C.

Proceeding as in Example 4, Step (c), but replacing piperidine with diethylamine, gave 1-(4-amino-5-chloro-2-methoxyphenyl)-5-diethylamino-pentan-1-one hydrochloride, m.p. 178°–179° C.

Proceeding as in Example 4, Step (c), but replacing piperidine with di(prop-1-yl)amine, gave 1-(4-amino-5-chloro-2-methoxyphenyl)-5-di(prop-1-yl)-aminopentan-1-one hydrochloride, m.p. 162°–165° C.

Proceeding as in Example 4, Step (c), but replacing piperidine with pyrrolidine, gave 1-(4-amino-5-chloro-2-methoxyphenyl)-5-(pyrrolidin-1-yl)-pentan-1-one hydrochloride, m.p. 203°–205° C.

Proceeding as in Example 4, Step (c), but replacing piperidine with 4-methylpiperidine, gave 1-(4-amino-5-chloro-2-methoxyphenyl)-5-(4-methyl-piperidin-1-yl)pentan-1-one hydrochloride, m.p. 195°–197° C.

Proceeding as in Example 4, Step (c), but replacing piperidine with 4,4-dimethylpiperidine, gave 1-(4-amino-5-chloro-2-methoxyphenyl)-5-(4,4-dimethylpiperidin-1-yl)pentan-1-one hydrochloride, m.p. 239°–241° C.

Proceeding as in Example 4, Step (c), but replacing piperidine with 4-ethylpiperidine, gave 1-(4-amino-5-chloro-2-methoxyphenyl)-5-(4-ethyl-piperidin-1-yl)pentan-1-one hydrochloride, m.p. 197°–198° C.

Proceeding as in Example 4, Step (c), but replacing piperidine with 4-(prop-1-yl)piperidine, gave 1-(4-amino-5-chloro-2-methoxyphenyl)-5-(4-(prop-1-yl)piperidin-1-yl]pentan-1-one hydrochloride, m.p. 212°–213° C.

Proceeding as in Example 4, Step (c), but replacing piperidine with 4-aminocarbonylpiperidine, gave 1-(4-amino-5-chloro-2-methoxyphenyl)-5-(4-aminocarbonylpiperidin-1-yl)pentan-1-one hydrochloride, m.p. 230°–235° C.

Proceeding as in Example 4, Step (c), but replacing piperidine with 4-hydroxypiperidine, gave 1-(4-amino-5-chloro-2-methoxyphenyl)-5-(4-hydroxy-piperidin-1-yl)pentan-1-one hydrochloride, m.p. 205°–207° C.

Proceeding as in Example 4, Step (c), but replacing piperidine with 4-methoxypiperidine, gave 1-(4-amino-5-chloro-2-methoxyphenyl)-5-(4-methoxy-piperidin-1-yl)pentan-1-one hydrochloride, m.p. 193°–195° C.

Proceeding as in Example 4, Step (c), but replacing piperidine with 4-(methylsulfonyl)aminopiperidine, gave 1-(4-amino-5-chloro-2-methoxyphenyl)-5-[4-(methylsulfonyl)aminopiperidin-1-yl]pentan-1-one hydrochloride, m.p. 245°–246° C.

Proceeding as in Example 4, Step (c), but replacing piperidine with 4-(methylsulfonyl)aminomethylpiperidine, gave 1-(4-amino-5-chloro-2-methoxy-phenyl)-5-[4-(methylsulfonyl)aminomethylpiperidin-1-yl]pentan-1-one hydrochloride, m.p. 231°–232° C.

Proceeding as in Example 4, Step (c), but replacing piperidine with 4-phenylpiperidine, gave 1-(4-amino-5- chloro-2-methoxyphenyl)-5-(4-phenyl-piperidin-1-yl) pentan-1-one hydrochloride, m.p. 257°–259° C.

Proceeding as in Example 4, Step (c), but replacing piperidine with morpholine, gave 1-(4-amino-5-chloro-2-methoxyphenyl)-5-(morphol-1-yl)-pentan-1-one hydrochloride, m.p. 229°–231° C.

Proceeding as in Example 4, Step (c), but replacing piperidine with azacycloheptane, gave 1-(4-amino-5-chloro-2-methoxyphenyl)-5-(azacyclo-hept-1-yl)pentan-1-one hydrochloride, m.p. 203°–205° C.

Proceeding as in Example 4, Step (c), but replacing piperidine with 3-azabicyclo[2.2.]heptane, gave 1-(4-amino-5-chloro-2-methoxyphenyl)-5-(3-azabicyclo[2.2.]hept-3-yl) pentan-1-one hydrochloride, m.p. 158°–160° C.

Proceeding as in Example 4, Step (c), but replacing 1-(4-acetylamino-5-chloro-2-methoxyphenyl)-5-chloropentan-1-one with 1-[4-acetylamino-5-chloro-2-(4-methoxybenzyloxy)phenyl]-5-chloropentan-1-one, gave 1-[4-amino-5-chloro-2-(4-methoxybenzyloxy)phenyl]-5-(piperidin-1-yl)pentan-1-one hydrochloride, m.p. 229°–230° C.

Proceeding as in Example 4, Step (c), but replacing 1-(4-acetylamino-5-chloro-2-methoxyphenyl)-5-chloropentan-1-one with 1-[4-acetylamino-5-chloro-2-(3,4-dimethoxy)benzyloxyphenyl]-5-chloro-pentan-1-one, gave 1-[4-amino-5-chloro-2-(3,4-dimethoxybenzyloxy)phenyl]-5-(piperidin-1-yl)pentan-1-one, m.p. 125°–127° C.

Proceeding as in Example 4, Step (c), but replacing 1-(4-acetylamino-5-chloro-2-methoxyphenyl)-5-chloropentan-1-one with 1-[4-acetylamino-5-chloro-2-(3,4-methylenedioxybenzyloxy)phenyl]-5-chloropentan-1-one, gave 1-[4-amino-5-chloro-2-(3,4-methylenedioxybenzyloxy)phenyl]-5-(piperidin-1-yl)pen. tan-1-one, m.p. 120°–122° C.

Proceeding as in Example 4, Step (c), but replacing 1-(4-acetylamino-5-chloro-2-methoxyphenyl)-5-chloropentan-1-one with 1-[4-acetylamino-5-chloro-2-(3,5-dimethoxybenzyloxy)phenyl]-5-chloropentan-1-one and piperidine with dimethylamine, gave 1-[4-amino-5-chloro-2-(3,5-dimethoxybenzyloxy)phenyl]-5-dimethylaminopentan-1-one hydrochloride, m.p. 221°–224° C.

Proceeding as in Example 4, Step (c), but replacing 1-(4-acetylamino-5-chloro-2-methoxyphenyl)-5-chloropentan-1-one with 1-[4-acetylamino-5-chloro-2-(3,5-dimethoxybenzyloxy)phenyl]-5-chloropentan-1-one and piperidine with diethylamine, gave 1-[4-amino-5-chloro-2-(3,5-dimethoxybenzyloxy)phenyl]-5-diethylaminopentan-1-one, m.p. 105°–107° C.

Proceeding as in Example 4, Step (c), but replacing 1-(4-acetylamino-5-chloro-2-methoxyphenyl)-5-chloropentan-1-one with 1-[4-acetylamino-5-chloro-2-(3,5-dimethoxybenzyloxy)phenyl]-5-chloro-pentan-1-one and piperidine with pyrrolidine, gave 1-[4-amino-5-chloro-2-(3,5-dimethoxybenzyloxy)phenyl]1-5-(pyrrolidin-1-yl)pentan-1-one, m.p. 125–127° C.

Proceeding as in Example 4, Step (c), but replacing 1-(4-acetylamino-5-chloro-2-methoxyphenyl)-5-chloropentan-1-one with 1-[4-acetylamino-5-chloro-2-(3,5-dimethoxybenzyloxy)phenyl]-5-chloropentan-1-one, gave 1-[4-amino-5-chloro-2-(3,5-dimethoxybenzyloxy)phenyl]-5-(piperidin-1-yl)pentan-1-one, m.p. 128–130° C.

Proceeding as in Example 4, Step (c), but replacing 1-(4-acetylamino-5-chloro-2-methoxyphenyl)-5-chloropentan-1-one with 1-(4-acetylamino-5-bromo-2-(3,5-dimethoxy)benzyloxyphenyl]-5-bromopentan-1-one, gave 1-(4-amino-5-bromo-2-(3,5-dimethoxy)benzyloxyphenyl]-5-(piperdin-1-yl)pentan-1-one hydrochloride, m.p. 238–239° C.

Proceeding as in Example 4, Step (c), but replacing 1-(4-acetylamino-5-chloro-2-methoxyphenyl)-5-chloropentan-1-one with 1-[4-acetylamino-5-chloro-2-(3,5-dimethoxybenzyloxy)phenyl]-5-chloropentan-1-one and piperidine with 4-methylpiperidine, gave 1-[4-amino-5-chloro-2-(3,5-dimethoxybenzyloxy)phenyl]-5-(4-methylpiperidin-1-yl)pentan-1-one, m.p. 136–137° C.

Proceeding as in Example 4, Step (c), but replacing 1-(4-acetylamino-5-chloro-2-methoxyphenyl)-5-chloropentan-1-one with 1-[4-acetylamino-5-chloro-2-(3,5-dimethoxybenzyloxy)phenyl]-5-chloropentan-1-one and piperidine with 4-(prop-1-yl)piperidine, gave 1-[4-amino-5-chloro-2-(3,5-dimethoxybenzyloxy)-phenyl]-5-[4-(prop-1-yl)piperidin-1-yl]pentan-1-one, m.p. 119–120° C.

Proceeding as in Example 4, Step (c), but replacing 1-(4-acetylamino-5-chloro-2-methoxyphenyl)-5-chloropentan-1-one with 1-[4-acetylamino-5-chloro-2-(3,5-dimethoxybenzyloxy)phenyl]-5-chloropentan-1-one and piperidine with 4,4-dimethylpiperidine, gave 1-[4-amino-5-chloro-2-(3,5-dimethoxybenzyloxy)-phenyl]-5-(4,4-dimethylpiperidin-1-yl)pentan-1-one, m.p. 135–136° C.

Proceeding as in Example 4, Step (c), but replacing 1-(4-acetylamino-5-chloro-2-methoxyphenyl)-5-chloropentan-1-one with 1-[4-acetylamino-5-chloro-2-(3,5-dimethoxybenzyloxy)phenyl]-5-chloropentan-1-one and piperidine with 4-hydroxypiperidine, gave 1-[4-amino-5-chloro-2-(3,5-dimethoxybenzyloxy)-phenyl]-5-(4-hydroxypiperidin-1-yl)pentan-1-one hydrochloride, m.p. 220–222° C.

Proceeding as in Example 4, Step (c), but replacing 1-(4-acetylamino-5-chloro-2-methoxyphenyl)-5-chloropentan-1-one with 1-[4-acetylamino-5-chloro-2-(3,5-dimethoxybenzyloxy)phenyl]-5-chloropentan-1-one and piperidine with 4-(2-hydroxyethyl)piperidine, gave 1-[4-amino-5-chloro-2-(3,5-dimethoxy-benzyloxy)phenyl]-5-[4-(2-hydroxyethyl)piperidin-1-yl]pentan-1-one hydrochloride, m.p. 180–183° C.

Proceeding as in Example 4, Step (c), but replacing 1-(4-acetylamino-5-chloro-2-methoxyphenyl)-5-chloropentan-1-one with 1-[4-acetylamino-5-chloro-2-(3,5-dimethoxybenzyloxy)phenyl]-5-chloro-pentan-1-one and piperidine with 4-methoxypiperidine, gave 1-[4-amino-5-chloro-2-(3,5-dimethoxybenzyloxy)phenyl]-5-(4-methoxypiperidin-1-yl)pentan-1-one hydrochloride, m.p. 195–196° C.

Proceeding as in Example 4, Step (c), but replacing 1-(4-acetylamino-5-chloro-2-methoxyphenyl)-5-chloropentan-1-one with 1-[4-acetylamino-5-chloro-2-(3,5-dimethoxybenzyloxy)phenyl]-5-chloropentan-1-one and piperidine with 4-aminocarbonylpiperidine, gave 1-[4-amino-5-chloro-2-(3,5-dimethoxybenzyloxy)-phenyl]-5-(4-aminocarbonylpiperidin-1-yl)pentan-1-one hydrochloride, m.p. 207–209° C.

Proceeding as in Example 4, Step (c), but replacing 1-(4-acetylamino-5-chloro-2-methoxyphenyl)-5-chloropentan-1-one with 1-[4-acetylamino-5-chloro-2-(3,5-dimethoxybenzyloxy)phenyl]-5-chloropentan-1-one and piperidine with 4-(aminocarbonyl)aminopiperidine, gave 1-[4-amino-5-chloro-2-(3,5-dimethoxy-benzyloxy)phenyl]-5-[4-(aminocarbonyl)aminopiperidin-1-yl]pentan-1-one hydrochloride, m.p. 220°–224° C.

Proceeding as in Example 4, Step (c), but replacing 1-[4-acety-lamino-5-chloro-2-methoxyphenyl)-5-chloropentan-1-one with 1-[4-acetylaminco-5-chloro-2-[3,5-dimethoxybenzyloxy)phenyl]-5-chloropentan-1-one and piperidine with 4-(aminocarbonyl)aminomethylpiperidine, gave 1-[4-amino-5-chloro-2-(3,5-dimethoxybenzyloxy)

phenyl]-5-[4-(aminocarbonyl)aminomethyl-piperidin-1-yl] pentan-1-one hydrochloride, m.p. 130°–1350° C.

Proceeding as in Example 4, Step (c), but replacing 1-(4-acetylamino-5-chloro-2-methoxyphenyl)-5-chloropentan-1-one with 1-[4-acetylaminco-5-chloro-2-(3,5-dimethoxybenzyloxy) phenyl]-5-chloropentan-1-one and piperidine with 4-(methylsulfonyl)aminopiperidine, gave 1-[4-amino-5-chloro-2-(3,5-dimethoxy-benzyloxy) phenyl]-5-[4-(methylsulfonyl)aminopiperidin-1-yl]pentan-1-one hydrochloride, m.p. 240°–245° C.

Proceeding as in Example 4, Step (c), but replacing 1-(4-acetylamino-5-chloro-2-methoxyphenyl)-5-chloropentan-1-one with 1-[4-acetylamino-5-chloro-2-(3,5-dimethoxybenzyloxy) phenyl]-5-chloropentan-1-one and piperidine with 4-(methylsulfonyl)aminomethylpiperidine, gave 1-[4-amino-5-chloro-2-(3,5-dimethoxybenzyloxy) phenyl]-5-[4-(methylsulfonyl) aminomethyl-piperidin-1-yl] pentan-1-one hydrochloride, m.p. 211°–213° C.

Proceeding as in Example 4, Step (c), but replacing 1-(4-acetylamino-5-chloro-2-methoxyphenyl)-5-chloropentan-1-one with 1-[4-acetylamino-5-chloro-2-(3,5-dimethoxybenzyloxy) phenyl]-5-chloropentan-1-one and piperidine with 4[2-(methylsulfonyl)aminoethylpiperidine, gave 1-[4-amino-5-chloro-2-(3,5-dimethoxybenzyloxy) phenyl]-5-{4-[2-(methylsulfonyl)aminoethyl]-piperidin-1-yl}pentan-1-one hydrochloride, m.p. 205°–206° C.

Proceeding as in Example 4, Step (c), but replacing 1-(4-acetylamino-5-chloro-2-methoxyphenyl)-5-chloropentan-1-one with 1-[4-acetylamino-5-chloro-2-(3,5-dimethoxybenzyloxy) phenyl)-5-chloropentan-1-one and piperidine with 4-phenylpiperidine, gave 1-[4-amino-5-chloro-2-(3,5-dimethoxybenzyloxy) phenyl]-5-(4-phenylpiperidin-1-yl)pentan-1-one hydrochloride, m.p. 237°–239 C.

Proceeding as in Example 4, Step (c), but replacing 1-4-acetylamino-5-chloro-2-methoxyphenyl)-5-chloropentan-1-one with 1-[4-acetylamino-5-chloro-2-(3,5-dimethoxybenzyloxy) phenyl]-5-chloropentan-1-one and piperidine with azacycloheptane, gave 1-[4-amino-5-chloro-2-(3,5-dimethoxybenzyloxy) phenyl]-5-(azacyclohept-1-yl) pentan-1-one, m.p. 137°–139° C.

Proceeding as in Example 4, Step (c), but replacing 1-(4-acetylamino-5-chloro-2-methoxyphenyl)-5-chloropentan-1-one with 1-{4-acetylamino-5-chloro-2-[2-(4-methoxyphen)ethoxy]phenyl}-5-chloropentan-1-one, gave 1-{4-amino-5-chloro-2-[2-(4-methoxyphen) ethoxy] phenyl}-5-(piperidin-1-yl)pentan-1-one, m.p. 211°–212° C.

Proceeding as in Example 4, Step (c), but replacing 1-(4-acetylamino-5-chloro-2-methoxyphenyl)-5-chloropentan-1-one with 1-{4-acetylamino-5-chloro-2-[2-(3,4-dimethoxyphen)ethoxy]phenyl}-5-chloropentan-1-one, gave 1-{4-amino-5-chloro-2-[2-(3,4-dimethoxyphen) ethoxy]phenyl}-5-(piperidin-1-yl)pentan-1-one, m.p. 224°–225° C.

Proceeding as in Example 4, Step (c), but replacing 1-(4-acetylamino-5-chloro-2-methoxyphenyl)-5-chloropentan-1-one with 1-{4-acetylamino-5-chloro-2-[2-(4-methoxyphen)ethoxy]phenyl}-5-chloropentan-1-one and piperdine with 4-methylpiperidine, gave 1-{4-amino-5-chloro-2-[2-(4-methoxyphen) ethoxy]-phenyl}-5-(4-methylpiperidin-1-yl)pentan-1-one hydrochloride, m.p. 226°–228° C.

Example 5

4'-Amino-5'-chloro-2'-methoxyacetophenone

The following is the preparation of a compound of Formula VIII in which $R^1$ is chloro, $R^2$ is hydrogen and $R^3$ is methoxy.

N-Methoxy-N-methyl-4-amino-5-chloro-2-methoxybenzamide (24.4 g, 100 mmol) was dissolved in THF (400 mL) and the solution was cooled to −400° C. Methyl-lithium in ether (143 mL, 4.4 g, 200 mmol) ) was added and the mixture was allowed to warm to 0° C. Aqueous hydrochloric acid was added and the mixture was extracted into ethyl acetate. The extract was washed with brine, dried over sodium sulfate, and evaporated to leave a solid. Crystallization from ethyl acetate-hexane gave 4'-amino-5'-chloro-2'-methoxyacetophenone (15.0 g, 75 mmol), m.p. 114°–116° C.

Proceeding as in Example 5, but replacing N-methoxy-N-methyl-4-amino-5-chloro-2-methoxybenzamide with N-methoxy-N-methyl-4-amino-5-chloro-2,3-ethylenedioxybenzamide gave 4-amino-5-chloro-2,3-ethylenedioxyphenyl-acetophenone, m.p. 133°–135° C.

Proceeding as in Example 5, but replacing N-methoxy-N-methyl-4-amino-5-chloro-2-methoxybenzamide with N-methoxy-N-methyl-4-amino-5-chloro-2,3-dimethoxybenzamide gave 4-amino-5-chloro-2,3-dimethoxyphenylacetophenone, map. 75°–78° C.

Example 6

4'-Amino-5'-chloro-2'3'-ethylenedioxyacetophenone

The following is the preparation of a compound of Formula VI in which $R^1$ is chloro and $R^2$ and $R^3$ are together ethylenedioxy.

Step (a)

A solution of 1,4-benzodioxan (8.4M, 25 mL, 0.21 mol) in 15 mL of acetic acid was treated with chlorine gas at 10°–20° C. giving a yellow precipitate. The precipitate was isolated by filtration and washed with water. Crystallization of the precipitate from ethanol gave 6,7-dichloro-1,4-benzodioxane (25.5 g, 0.124 mol), m.p. 147°–148° C.

Step (b)

A mixture of 6,7-dichloro-1,4-benzodioxane (10.25 g, 0.05 mol), acetyl chloride (13.5M, 5 mL, 0.0675 mol) and aluminum chloride (10 g, 0.075 mol) in 200 mL of 1,2-dichloroethane was stirred under nitrogen for 24 hours. The mixture was poured into approximately 500 mL of ice/dilute hydrochloric acid and extracted with methylene chloride. The methylene chloride extract were washed with sodium bicarbonate (1x), water (1x) and brine (1x) and then dried over sodium sulfate. The methylene chloride was filtered and concentrated by rotary evaporation. Purification of the residue by column chromatography (silica 230–400 mesh; 15% ethyl acetate/hexane) gave 5,6-dichloro-2,3-ethylenedioxy-acetophenone (8.1 g, 0.033 mo), m.p. 83°–86° C.

Step (c)

5',6'-Dichloro-2',3'-ethylenedioxyacetophenone (8.5 g, 0.0344 miol) was added in portions to 34.5 mL of stirring fuming nitric acid at a rate such that the temperature of the reaction mixture remained below 10° C. The mixture was stirred for an additional 10 minutes at 5 C. and then poured onto 250 g of crushed ice giving yellow precipitate. The precipitate was isolated by filtration and washed with water. Drying gave 5',6'-dichloro-2',3'-ethylenedioxy-4'-nitroacetophenone (8.9 g, 0.0341 mol), m.p. 181°–182° C.

Step (d)

A mixture of 5',6'-dichloro-2',3'-ethylenedioxy-4'-nitroacetophenone (2 g, 7.63 mmol) and 10% palladium on carbon (800 mg) in 17 mL of 15% sodium hydroxide and 160 mL of ethanol hydrogenated at 57 psi for 7 hours. The mixture was filtered and concentrated by rotary evaporation and the residue was stirred into water. Drying gave 4'-amino-2',3'-ethylenedioxyacetophenone (970 mg, 5.04 mmol), m.p. 135°–136° C.

Step (e)

A solution of 4'-amino-2',3'-ethylenedioxyacetophenone (310 mg, 1.60 mmol) in 2.3 mL of pyridine under nitrogen was cooled in an ice/water bath and 6.9 mL of acetic anhydride was added drop-wise. The mixture was allowed to warm to room temperature and then stirred for 16 hours. The mixture was concentrated by rotary evaporation and the residue was stirred into water. The residue was isolated by filtration and washed with water. Drying gave 2',3'-ethylenedioxy-4'-(methylcarbonylamino)acetophenone (289 mg, 1.23 mmol), m.p. 142°–144° C.

Step (f)

A solution of 2',3'-ethylenedioxy-4'-(methylcarbonylamino)acetophenone (250 mg, 1.06 mmol) in 6 mL of dimethylformamide under nitrogen was cooled in an ice/water bath and N-chlorosuccinimide (156 mg, 1.17 mmol) was added. The mixture was allowed to warm to room temperature and then heated at 55° C. for 1.5 hours. The mixture was then cooled to room temperature and stirred for 16 hours. The mixture was concentrated by rotary evaporation and the residue was stirred into water. The residue was isolated by filtration and washed with water. Drying gave 5'-chloro-2',3'-ethylenedioxy-4'-(methylcarbonylamino)-acetophenone (170 mg, 0.69 mmol), m.p. 181°–182° C.

Step (g)

A mixture of 5'-chloro-2',3'-ethylenedioxy-4'-(methylcarbonylamino)-acetophenone (152 mg, 0.56 mmol) and sodium hydroxide (4N, 1.4 mL, 5.6 mmol) in 5 mL of methanol was heated at reflux for 3.5 hours. The mixture was concentrated by rotary evaporation and the residue was stirred into water. The residue was isolated by filtration and washed with water. Drying gave 4'-amino-5'-chloro-2',3'-ethylenedioxyacetophenone (95 mg, 0.41 mmol), m.p. 133°–136° C.

Example 7

1-(4-Amino-5-chloro-2-methoxyphenyl)-3-(piperidin-4-yl)propan-1-one

The following is the preparation of a compound of Formula I in which $R^1$ is chloro, $R^3$ is methoxy, $R^4$ is a group of Formula (b) in which p is 0, q is 2, and $R^7$ is hydrogen.

Step (a)

4-Amino-5-chloro-2-methoxyacetophenone (12.75 g, 64 mmol), prepared as in Example 5, was suspended in THF (125 mL). The suspension was added to a −50° C. solution of lithium diisopropylamide (16.1 g, 150 mmol) in THF (200 mL) and the mixture was stirred at 0° C. for 15 minutes. Pyridine-4-carboxaldehyde (8.0 g, 75 mmol) was added and the mixture was allowed to warm to 5° C. Aqueous ammonium chloride was added and the mixture was extracted three times with ethyl acetate. The combined extracts were washed with water, dried over sodium sulfate, and concentrated in vacuo to leave a semi-solid residue. Ethyl acetate-hexane was added and filtration gave 1-(4-amino-5-chloro-2-methoxyphenyl)-3-hydroxy-3-(pyridin-4-yl)propan-1-one (12.1 g, 40 mmol), m.p. 181°–183° C.

Step (b)

1-(4-Amino-5-chloro-2-methoxyphenyl)-3-hydroxy-3-(pyridin-4-yl)-propan-1-one (8.6 g, 28 mmol), prepared as in Example 6, Step (a), was dissolved in concentrated sulfuric acid (40 mL) and the solution was stirred at room temperature for 15 minutes. The solution was poured onto ice, basified with ammonium hydroxide, and then filtered to collect a yellow solid. Drying gave 1-(4-amino-5-chloro-2-methoxyphenyl)-3-(pyridin-4-yl)-2-propen-1-one (7.6 g, 26 mmol), 209°–211° C.

Step (c)

1-(4-Amino-5-chloro-2-methoxyphenyl)-3-(pyridin-4-yl)-2-propen-1-one (0.5 g, 1.7 mmol), prepared as in Example 6, Step (b), was dissolved in acetic acid (25 mL) and the solution was hydrogenated over 5% rhodium-alumina catalyst (0.2 g) at 50 psi for 24 hours. The solution was filtered, diluted with water, basified with ammonium hydroxide, and extracted three times with methylene chloride. The combined extracts were dried over sodium sulfate. Evaporation gave 1-(4-amino-5-chloro-2-methoxyphenyl)-3-(piperidin-4-yl)propan-1-one (0.35 g, 1.2 mmol).

Example 8

1-(4-Amino-5-chloro-2-methoxyphenyl)-3-(piperidin-4-yl)-2-propen-1-one

The following is an alternative method to Example 7, Steps (a)–(b).

Potassium hydroxide (5.0 g, 89.3 mmol) was dissolved in water (25.0 mL). Ethanol (100 mL) was added to the solution and the mixture was stirred. 4-Amino-5-chloro-2-methoxyacetophenone (10.0 g, 50.5 mmol), prepared as in Example 5, was added to the stirring solution and after 5 minutes pyridine-4-carboxaldehyde (6.4 g, 60.0 mmol) was added and the mixture was stirred for approximately 12 hours. The mixture was then diluted with water and filtered to collect a yellow solid. Drying gave 1-(4-amino-5-chloro-2-methoxyphenyl)-3-(pyridin-4-yl)-2-propen-1-one (12.85 g, 44.5 mmol).

Proceeding as in Example 8, but replacing 4-amino-5-chloro-2-methoxyacetophenone with 4-amino-5-chloro-2,3-ethylenedioxy-acetophenone gave 1-(4-amino-5-chloro-2,3-ethylenedioxyphenyl)-3-(pyridin-4-yl)propen-1-one, m.p. 209°–211° C. 5 Proceeding as in Example 8, but replacing 4-amino-5-chloro-2-methoxyacetophenone with 4-amino-5-chloro-2,3-dimethoxy-acetophenone gave 1-(4-amino-5-chloro-2,3-dimethoxyphenyl)-3-(pyridin-4-yl)-propen-1-one, m.p. 220°–223° C.

Example 9

1-(4-Amino-5-chloro-2,3-ethylenedioxyphenyl)-3-(pipe

The following is an alternative method to Example 7, St

Step (a)

A solution of 1-(4-amino-5-chloro-2,3-ethylenedioxyphenyl)-3-(pyridin-4-yl)-2-propen-1-one (1.55 g, 5 mmol) in 50 mL of THF was hydrogenated over 5% palladium on carbon (0.5 g) for approximately 2 hours. The mixture was filtered and concentrated by rotary evaporation. Purification of the residue by silica gel chromatography (2% $CH_3OH$—$CH_2$+0.1% $NH_4OH$) gave 1-(4-amino-5-chloro-2,3-ethylenedioxyphenyl)-3-(pyridin-4-yl)propan.-1-one (1.23 g, 3.8 mmol)

Step (b)

A solution of 1-(4-amino-5-chloro-2,3-ethylenedioxyphenyl)-3-(pyridin-4-yl) propan-1-one (1.23 g, 3.8 mmol) in 15 mL of glacial acetic acid was hydrogenated over 5% rhodium-alumina catalyst (1.0 g) at 50 psi for approximately 20 hours. The mixture was filtered and the filter was washed several times with ethanol. The combined filtrates were concentrated in vacuo. Purification of the residue by silica gel chromatography (20% $CH_3OH$—$CH_2Cl_2$+0.2% $NH_4OH$) gave 1-(4-amino-5-chloro-2,3-ethylenedioxyphenyl)-3-(pyridin-4-ylpiperidin-4-yl)- (0.22 g, 0.68 mmol).

Example 10

1-(4-Amino-5-chloro-2-methoxyphenyl)-3-[1-(prop-1-yl)piperidin-4-yl ]propan-1-one The following is the preparation of a compound of Formula I in which $R^1$ is chloro, $R^3$ is methoxy, and $R^4$ is a group of Formula (b), in which p is 0, q is 2 and $R^7$ is prop-1-yl.

1-(4-Amino-5-chloro-2-methoxyphenyl)-3-(piperidin-4-yl)propan-1-one (0.2 g, 0.67 mmol), prepared as in Example 3 or Example 7, triethylamine (0.2 mL), and 1-bromopropane (0.065 mL, 0.75 mmol) were dissolved in DMF (4 mL) and the solution was stirred at room temperature for 12 hours. The solution was partitioned between aqueous ammonium hydroxide and ethyl acetate. The ethyl acetate layer was separated, washed with water and then brine, dried over sodium sulfate, and evaporated. Purification of the residue by silica gel chromatography (10% $CH_3OH$—$CH_2Cl_2$) gave 1-(4-amino-5-chloro-2-methoxyphenyl)-3-(1-(prop-1-yl) piperidin-4-yl]propan-1-one which was then dissolved in ethanolic hydrochloric acid. Crystallization with ether gave 1-(4-amino-5-chloro-2-methoxyphenyl)-3-[1-(prop-1-yl) piperidin-4-yl]propan-1-one hydrochloride (0.15 g, 0.4 mmol), m.p. 200°–201° C.

Proceeding as in Example 10, but replacing 1-bromopropane with iodomethane, gave 1-(4-amino-5-chloro-2-methoxyphenyl)-3-(1-methylpiperidin-4-yl)propan-1-one hydrochloride, m.p. 179°–180 C.

Proceeding as in Example 10, but replacing 1-bromopropane with iodoethane, gave 1-(4-amino-5-chloro-2-methoxyphenyl)-3-(1-ethylpiperidin-4-yl)propan-1-one hydrochloride, m.p. 128°–130° C.

Proceeding as in Example 10, but replacing 1-bromopropane with iodobutane, gave 1-(4-amino-5-chloro-2-methoxyphenyl)-3-[1-(but-1-yl) piperidin-4-yl]-propan-1-one hydrochloride, m.p. 195°–196° C.

Proceeding as in Example 10, but replacing 1-bromopropane with 1-bromo-2-methylpropane, gave 1-(4-amino-5-chloro-2-methoxyphenyl)-3-(1-(2-methyl-prop-1-yl) piperidin-4-yl]propan-1-one hydrochloride, m.p. 198°–199° C.

Proceeding as in Example 10, but replacing 1-bromopropane with 1-bromo-3-methylbutane, gave 1-(4-amino-5-chloro-2-methoxyphenyl)-3-[1-(3-methyl-but-1-yl) piperidin-4-yl]propan-1-one hydrochloride, m.p. 178°–179° C.

Proceeding as in Example 10, but replacing 1-bromopropane with 1-bromopentane, gave 1-(4-amino-5-chloro-2-methoxyphenyl)-3-[1-(pent-1-yl)-piperidin-4-yl] propan-1-one hydrochloride, m.p. 196°–197° C.

Proceeding as in Example 10, but replacing 1-bromopropane with 1-bromohexane, gave 1-(4-amino-5-chloro-2-methoxyphenyl)-3-[1-(hex-1-yl)-piperidin-4-yl] propan-1-one hydrochloride, m.p. 212°–213° C.

Proceeding as in Example 10, but replacing 1-bromopropane with 3-bromopropene, gave 1-(4-amino-5-chloro-2-methoxyphenyl)-3-[1-(2-propenyl)-piperidin-4-yl] propan-1-one hydrochloride, m.p. 162°–163° C.

Proceeding as in Example 10, but replacing 1-bromopropane with 1-chloro-2-methoxyethane, gave 1-(4-amino-5-chloro-2-methoxyphenyl)-3-[1-(2-methoxyethane)piperidin-4-yl]propan-1-one hydrochloride.

Proceeding as in Example 10, but replacing 1-bromopropane with 2-bromo-1-[(dimethylaminosulfonyl) amino]ethane, gave 1-(4-amino-5-chloro-2-methoxyphenyl)-3-{1-[2-(dimethylaminosulfonyl)aminoethane]piperidin-4-yl}propan-1-one hydrochloride, m.p. 195°–196° C.

Proceeding as in Example 10, but replacing 1-bromopropane with 2-bromo-1-[(dimethylaminocarbonyl) amino]ethane, gave 1-(4-amino-5-chloro-2-methoxyphenyl)-3-{1-[2-(dimethylaminocarbonyl)aminoethyl] piperidin-4-yl}propan-1-one hydrochloride, m.p. 167°–171° C.

Proceeding as in Example 10, but replacing 1-bromopropane with 2-bromo-1-[(methoxycarbonyl) amino]ethane, gave 1-(4-amino-5-chloro-2-methoxyphenyl)-3-{1-[2-(methoxycarbonyl)aminoethyl]piperidin-4-yl}propan-1-one hydrochloride, m.p. 239°–240° C.

Proceeding as in Example 10, but replacing 1-bromopropane with 2-bromo-1-[(trifluoromethylsulfonyl) amino]ethane, gave 1-(4-amino-5-chloro-2-methoxyphenyl)-3-{1-[2-(trifluoromethylsulfonyl)aminoethyl] piperidin-4-yl}propan-1-one hydrochloride, m.p. 235°–238° C.

Proceeding as in Example 10, but replacing 1-bromopropane with 3-bromo-1-[(methylsulfonyl)amino] propane, gave 1-(4-amino-5-chloro-2-methoxyphenyl)-3-{1-[3-(methylsulfonyl)aminoprop-1-yl]piperidin-4-yl}propan-1-one hydrochloride, m.p. 194°–195° C.

Proceeding as in Example 10, but replacing 1-bromopropane with iodobutane and 1-(4-amino-5-chloro-2-methoxyphenyl)-3-(piperidin-4-yl)propan-1-one with 1-(4-amino-5-chloro-2,3-ethylenedioxyphenyl)-3-(piperidin-4-yl)propan-1-one, gave 1-(4-amino-5-chloro-2,3-ethylenedioxyphenyl)-3-[1-(but-1-yl)-piperidin-4-yl] propan-1-one hydrochloride, m.p. 265°–267° C.

Proceeding as in Example 10, but replacing 1-bromopropane with iodobutane and 1-(4-amino-5-chloro-2-methoxyphenyl)-3-(piperidin-4-yl)propan-1-one with 1-(4-amino-5-chloro-2,3-dimethoxyphenyl)-3-(piperidin-4-yl)propan-1-one, gave 1-(4-amino-5-chloro-2,3-dimethoxyphenyl)-3-[1-(but-1-yl) piperidin-4-yl]-propan-1-one hydrochloride, m.p. 175°–176° C.

Example 11

1-(4-Amino-5-chloro-2-methoxyphenyl)-3-{1-(2-(methylsulfonyl)aminoethyl]piperidin-4-yl}propan-1-one The following is the preparation of a compound of Formula I in which $R^1$ is chloro, $R^3$ is methoxy, and $R^4$ is a group of Formula (b) in which p is 0, q is 2 and $R^7$ is 2-((methylsulfonyl)aminolethyl.

Ethylenimine (40 mg, 0.9 mmol) was dissolved in toluene (5 mL) and the solution was cooled in an ice bath. A solution of methanesulfonyl chloride in toluene (1 mL, 0.1 mg, 1 mmol) was slowly added and the mixture was stirred for 20 minutes to form a solution of 1-ethyleneimine.

1-(4-Amino-5-chloro-2-methoxyphenyl)-3-(piperidin-4-yl)propan-1-one (240 mg, 0.8 mmol), prepared as in Example 3 or Example 7, was dissolved in THF (20 mL), and the solution of 1-[2-(methylsulphonyl)ethyl] ethylenimine was added through a filter. The mixture was heated under reflux for 1 hour and then concentrated in vacuo. The residue was dissolved in ethyl acetate and this solution was then washed three times with water, dried over sodium sulfate, and evaporation. Purification by silica gel chromatography (15% $CH_3OH$—$CH_2Cl_2$) gave 1-(4-amino-5-chloro-2-methoxyphenyl)-3-{1-[2-(methylsulfonyl)

aminoethyl]-piperidin-4-yl}propan-1-one. Crystallization from ethanolic hydrochloric acid gave 1-(4-amino-5-chloro-2-methoxyphenyl)-3-{1-[2-(methylsulfonyl) aminoethyl]-piperidin-4-yl}propan-1-one hydrochloride, m.p. 123°–126° C.

Example 12

1-(4-Amino-5-chloro-2-(3,5-dimethoxybenzyloxy) phenyl]-3-{1-[2-(methylsulfonyl)aminoethyl] piperidin-4-yl)propan-1-one The following is the preparation of a compound of Formula I in which $R^1$ is chloro, $R^3$ is 3,5-dimethoxybenzyloxy and $R^4$ is a group of Formula (b), in which p is 0, q is 2 and $R^7$ is 2-(methylsulfonyl)aminoethyl.

Step (a)

1-[4-Amino-5-chloro-2-methoxyphenyl]-3-{1-[2-(methylsulfonyl) aminoethyl]-piperidin-4-yl}propan-1-one (1.19 g, 2.8 mmol), prepared as in Example 11, was dissolved in dichloroethane (50 mL). Boron tribromide in methylene chloride (4 mL, 1.0 g, 4.0 mmol) was added and the mixture was stirred for approximately 12 hours. The mixture was then poured over ice and methylene chloride (150 mL) and ammonium hydroxide) were added. This bilayer mixture was stirred until a solution had formed in the methylene chloride layer. The aqueous layer was removed and combined with fresh methylene chloride (100 mL) and this bilayer mixture was stirred. The methylene chloride layers were combined and dried over potassium carbonate. Filtration and concentration gave 1-(4-amino-5-chloro-2-hydroxyphenyl)-3-{1-[2-(methylsulfonyl)aminoethyl] piperidin-4-yl}propan-1-one (0.8 g, 2.0 -mmol)

Step (b)

1-[4-Amino-5-chloro-2-hydroxyphenyl)-3-{1-[2-(methylsulfonyl)aminoethyl]-piperidin-4-yl}propan-1-one (0.78 g, 1.93 mmol), 3,5-dimethoxybenzyl chloride (0.396 g, 2.12 mmol), and potassium carbonate (2.6 g, 18.8 mmol) were combined in DMF (-2 mL) and the mixture was stirred at ambient temperature for 48 hours. Additional 3,5-dimethoxybenzyl chloride (0.05 g, 0.13 mmol) was added and the mixture was stirred for 24 hours. The solvent was removed under reduced pressure and methylene chloride and aqueous sodium bicarbonate were added to the remaining solids and this bilayer mixture was stirred. The methylene chloride layer was separated, washed twice with water, and dried over potassium carbonate. Filtration and concentration gave a crude product (1.2 g).

Purification by silica gel chromatography (3% $CH_3OH$—$CH_2Cl_2$) gave 1- [4-amino-5-chloro-2-(3,5-dimethoxybenzyloxy)phenyl)-3-{1-(2-(methylsulfonyl) aminoethyl]-piperidin-4-yl}propan-1-one (0.53 g, 0.98 mmol). Crystallization from ethanolic hydrochloric acid gave 1-[4-amino-5-chloro-2-(3,5-dimethoxybenzyloxy) phenyl]-3-{1-[2-(methylsulfonyl)aminoethyl]-piperidin-4-yl}propan-1-one hydrochloride (0.54 g, 0.93 mmol), m.p. 123°–126° C.

Proceeding as in Example 12, Step (a), but replacing 1-[4-amino-5-chloro-2-methoxy-phenyl]-3-{1-[2-(methylsulfonyl)aminoeth yl]piperidin-4-yl}propan-1-one with 1-(4-amino-5-chloro-2-methoxyphenyl)-3-(1-(but-1-yl)piperidin-4-yl]-propan-1-one, and then correspondingly as in Example 12, Step (b), gave 1-[4-amino-5-chloro-2-(3,5-dimethoxybenzyloxy)phenyl]-3-[1-(but-1-yl)-piperidin-4-yl]propan-1-one hydrochloride, m.p. 179°–182° C.

Proceeding as in Example 12, Step (a), but replacing 1-[4-amino-5-chloro-2-methoxyphenyl)-3-{1-(2-(methylsulfonyl)aminoethyl]piperidin-4-yl}propan-1-one with 1-[4-amino-5-chloro-2-methoxyphenyl)-3-(1-(pent-1-yl)piperidin-4-yl]-propa1-one, and then correspondingly as in Example 12, Step (b), gave 1-[4-amino-5-chloro-2-[3,5-dimethoxybenzyloxy)phenyl]-3-[1-(pent-1-yl)-piperidin-4-yl]propan-1-one hydrochloride, m.p. 174°–176° C.

Proceeding as in Example 12, but replacing 1-(4-amino-5-chloro-2-methoxy-phenyl]-3-{1-[2-(methylsulfonyl) aminoeth yl]piperidin-4-yl}propan-1-one with 1-[4-amino-5-chloro-2-methoxyphenyl)-3-(1-(2-methoxyethyl) piperidin-4-yl]-propan-1-one, and then correspondingly as in Example 12, Step (b), gave 1-[4-amino-5-chloro-2-(3,5-dimethoxybenzyloxy)phenyl]-3-[1-(2-methoxyethyl)-piperidin-4-yl]propan-1-one hydrochloride, m.p. 183°–184° C.

Proceeding as in Example 12, Step (a), but replacing 1-[4-amino-5-chloro-2-methoxyphenyl]-3-(I-[2-(methylsulfonyl)aminoeth yl]piperidin-4-yl)propan-1-one with 1-[4-amino-5-chloro-2-methoxyphenyl]-3-{1-[2-(dimethylaminosulfonyl)amino-ethyl]piperidin-4-yl}propan-1-one, and then correspondingly as in Example 12, Step (b), gave 1-4-amino-5-chloro-2-(3,5-dimethoxybenzyloxy)phenyl -3-(1-[2-(dimethylaminosulfonyl)aminoethyl]piperidin-4-yl}propan-1-on-e hydrochloride, m.p. 173°–176° C.

Proceeding as in Example 12, Step (b), but replacing 3,5-dimethoxybenzyl chloride with benzyl chloride, gave 1-(4-amino-5-chloro-2-benzyloxylhenyl)-3-{1-[2-(methylsulfonyl)aminoethyl]piperidin-4-yl}propan-1-one hydrochloride, m.p. 193°–194° C.

Proceeding as in Example 12, Step (b) but replacing 3,5-dimethoxybenzyl chloride with 3-methoxybenzyl chloride, gave 1-[4-amino-5-chloro-2-(3-methoxybenzyloxy)phenyl]-3-{1-[2-(methylsulfonyl)aminoethyl] piperidin-4-yl}propan-1-one hydrochloride, m.p. 174°–176° C.

Proceeding as in Example 12, Step (a), but replacing 1-(4-amino-5-chloro-2-methoxyphenyl)-3-{1-[2-(methylsulfonyl)aminoeth yl]piperidin-4-yl}propan-1-one with 1-[4-amino-5-chloro-2-methoxyphenyl]-5-(piperidin-1-yl)pentan-1-one, and then as in Example 12, Step (b), but replacing 3,5-dimethoxybenzyl chloride with iodoethane, gave 1-[4-amino-5-chloro-2-ethoxyphenyl]-5-(piperidin-1-yl)-pentan-1-one hydrochloride, m.p. 230°–231° C.

Proceeding as in Example 12, Step (a), but replacing 1-(4-amino-5-chloro-2-methoxyphenyl)-3-{1-[2-(methylsulfonyl)aminoeth yl]piperidin-4-yl}propan-1-one with 1-[4-amino-5-chloro-2-methoxyphen yl]-5-(piperidin-1-yl)pentan-1-one, and then as in Example 12, Step (b), but replacing 3,5-dimethoxybenzyl chloride with 1-bromopropane, gave 1-[4-amino-5-chloro-2-(prop-1-yloxy)phenyl]-5-(piperidin-1-yl)pentan-1-one hydrochloride, m.p. 232°–233° C.

Proceeding as in Example 12, Step (a), but replacing 1-(4-amino-5-chloro-2-methoxyphenyl)-3-{1-[2-(methylsulfonyl)aminoethyl]piperidin-4-ylpropan-1-one with 1-[4-amino-5-chloro-2-methoxyphenyl]-5-(piperidin-1-yl)pentan-1-one, and then as in Example 12, Step (b), but replacing 3,5-dimethoxybenzyl chloride with 3,5-dimethylbenzyl chloride, gave 1-[4-amino-5-chloro-2-(3,5-dimethylbenzyloxy)-phenyl]-5-(piperidin-1-yl)pentan-1-one hydrochloride, m.p. 218°–233° C.

Proceeding as in Example 12, Step (a), but replacing 1-[4-amino-5-chloro-2-methoxyphenyl)-3-{1-[2-(methylsulfonyl)aminoethyl]piperidin-4-yl}propan-1-one with 1-(4-amino-5-chloro-2-methoxyphenyl)-5-(4-aminocarbonylpiperidin-1-yl)-pentan-1-one, and then as in Example 12, Step (b), but replacing 3,5-dimethoxybenzyl chloride with 3-methoxybenzyl chloride, gave 1-[4-amino-5-chloro-2-(5-methoxybenzyloxy)phen yl]-5-(4-aminocarbonylpiperidin-1-yl)-pentan-1-one hydrochloride, m.p. 204°–205° C.

Example 13

1-(4-Amino-5-chloro-2-methoxyphenyl)-3-(1-[3-(4-methoxyphenyl)prop-1-yl]piperidin-4-yl}propan-1-one The following is the preparation of a compound of Formula I in which $R^1$ is chloro, $R^2$ is hydrogen and 3 is methoxy and $R^4$ is a group of Formula (b), in which p is 0, q is 2 and $R^7$ is 3-(4-methoxyphenyl)prop-1-yl.

Step (a)

A mixture of 1-(4-amino-5-chloro-2-methoxyphenyl)-3-pyridin-4-yl-propan-1-one (1.5 g, 5.16 mmol), prepared as in Example 3 or 7, 3-(4-methoxyphenyl)-1-iodopropane (1.64 g, 5.93 mmol) in 13 mL of acetonitrile was heated under nitrogen at reflux for approximately 4 hours. The mixture was concentrated in vacuo and purification of the residue by silica gel chromatography (5% CH$_3$OH—CH$_2$Cl$_2$+0.1% NH$^4$OH) gave 1-(4-amino-5-chloro-2-methoxyphenyl)-3-{1-[3-(4-methoxyphenyl)prop-1-yl)-pyridinyl-4-ylopropan-1-one hydroiodide (1.82 g, 3.28 mmol).

Step (b)

A solution of(4-amino-5-chloro-2-methoxyphenyl)-3-(1-[3-(4-methoxyphenyl)-prop-1-yl]pyridinyl-4-yl}propan-1-one hydroiodide (1.82 mg, 3.28 mmcl) in 30 mL of DMF was hydrogenated over a platinum(IV) oxide catalyst (350 mg) at 50 psi. The reaction mixture was filtered and concentrated under high vacuum. The residue was dissolved in 150 mL of methylene chloride and the solution was diluted with a solution of ammonium hydroxide. The methylene chloride layer was separated and washed with ice water (3x). The methylene chloride layer was dried over sodium sulfate and concentrated in vacuo. Crystallization of the residue from ethanolic hydrochloric acid gave 1-(4-amino-5-chloro-2-methoxy-phenyl)-3-{1-[3-(4-methoxyphenyl)prop-1-yl] piperidin-4-yl}propan-1-one hydrochloride (1.33 g, 3.09 mmol), m.p. 188°–190° C.

Proceeding as in Example 13, Step (a), but replacing 3-(4-methoxyphenyl)-1-iodopropane with 3-(3,5-dimethoxyphenyl)-1-iodopropane, and then correspondingly as in Example 13, Step (b), gave 1-(4-amino-5-chloro-2-methoxy-phenyl)-3-{1-[3-(3,5-dimethoxyphenyl)prop-1-yl]piperidin-4-yl}propan-1-one hydrochloride, m.p. 160°–163° C.

Proceeding as in Example 13, Step (a), but replacing 3-(4-methoxyphenyl)-1-iodopropane with 3-(3,4-dimethoxyphenyl)-1-iodopropane, and then 2778-C.IP/52139 .01 correspondingly as in Example 13, Step (b), gave I-(4-amino-5-chloro-2-methoxy-phenyl)-3-{1-(3-(3,4-dimethoxyphenyl)prop-1-yl]piperidin-4-yl}propan-1-one hydrochloride, m.p. 177°–179° C.

Proceeding as in Example 13, Step (a), but replacing 3-(4-methoxyphenyl)-1-iodopropane with 3-(3,4-ethylenedioxyphenyl)-1-iodopropane, and then correspondingly as in Example 13, Step (b), gave 1-(4-amino-5-chloro-2-methoxy-phenyl)-3-{1-[3-(3,4-ethylenedioxyphenyl)prop-1-yl]piperidin-4-yl}propan-1-one hydrochloride, m.p. 168°–170° C.

Proceeding as in Example 13, Step (a), but replacing 3-(4-methoxyphenyl)-1-iodopropane with 3-(3,4-methylenedioxyphenyl)-1-iodopropane, and then correspondingly as in Example 13, Step (b), gave 1-(4-amino-5-chloro-2-methoxy-phenyl)-3-{1-[3-(3,4-methylenedioxyphenyl)prop-1-yl]piperidin-4-yl}propan-1-one hydrochloride, m.p. 200°–202° C.

Proceeding as in Example 13, Step (a), but replacing 3-(4-methoxyphenyl)-1-iodopropane with 3-(3,4,5-trimethoxyphenyl)-1-iodopropane, and then correspondingly as in Example 13, Step (b), gave 1-(4-amino-5-chloro-2-methoxy-phenyl)-3-{1-[3-(3,4,5-trimethoxyphenyl)prop-1-yl]piperidin-4-yl}propan-1-one hydrochloride, m.p. 180°–182° C.

Proceeding as in Example 13, Step (a), but replacing 1-(4-amino-5-chloro-2-methoxyphenyl)-3-pyridin-4-ylpropan-1-one with 1-(4-amino-5-chloro-2,3-ethylenedioxyphenyl)-3-pyridin-4-ylpropan-1-one, and then correspondingly as in Example 13, Step (b), gave 1-(4-amino-5-chloro-2,3-ethylenedioxyphenyl)-3-{1-(3-(4-methoxyphenyl)prop-1-yl]piperidin-4-yl }propan-1-one hydrochloride, m.p. 188°–189° C.

Example 14

1-(4-Amino-5-chloro-2-methoxyphenyl)-5-piperidin-1-ylpentan-1-one

The following is the preparation of a compound of Formula I in which $R^1$ is chloro, $R^2$ is hydrogen, $R^3$ is methoxy and $R^4$ is a group of Formula (a), in which p is 0, n is 4 and $R^5$ and $R^6$ together are piperdin-1-yl.

Step (a)

Magnesium (236 g, 9.71 mol) was suspended in 3.5 L of THF under nitrogen and 1-bromo-4-chlorobutane (1.11 L, 8.68M, 9.63 mol) was added at a rate such that the temperature of the mixture remained below 25° C. A solution of N-methoxy-N-methyl-4-amino-5-chloro-2-methoxybenzamide (400 g, 1.64 mol), prepared as in Example 2, under nitrogen in 4 L of THF was cooled to –20° C. and 410 mL of chlorotrimethylsilane was added. The mixture was allowed to warm to between –12 and 30° C. and then 2.5 L of the solution containing the magnesium and 1-bromo-2-chlorobutane was added over approximately 20 minutes. The mixture was cooled to 50° C. and then diluted with 420 mL of concentrated hydrochloric acid in 5 L of water. The mixture was heated to 32° C., stirred for 15 minutes and then diluted with approximately 2 L of ethyl acetate. The organic layer was separated and washed sequentially with 2 L of water and 2 L of 1:1 water/saturated sodium chloride solution and saturated sodium chloride solution. All aqueous layers were combined and extracted with ethyl acetate. All organic layers were combined, dried over sodium sulfate, filtered and concentrated. The residue was combined with hot hexane and allowed to stand at room temperature for approximately 12 hours giving a precipitate. The precipitate was isolated by filtration and washed with hexane. Drying in a vacuum oven at between 50 and 55° C. under a nitrogen gas bleed gave 1-(4-amino-5-chloro-2-methoxyphenyl)-5-chloropentan-1-one (365 g, 1.33 mol).

Step (b)

A mixture of 1-(4-amino-5-chloro-2-methoxyphenyl)-5-chloropentan-1-one (365 g, 1.33 mol), piperidine (620 g, 7 mol) and sodium iodide (30 g, 0.2 mol) in 1 L of DMF was heated at between 78 and 820° C. for 4 hours. The reaction mixture was allowed to cool to 500° C., then stirred for approximately 12 hours and 5 L of water was added. The mixture was stirred at 25°–30° C. for 1 hour giving a precipitate and the precipitate was isolated by filtration. The precipitate was washed with 4 L of water and dried under suction for 1 hour.

The precipitate was dissolved in approximately 2 L of ethyl acetate by heating to approximately 50° C. and then 130 mL of a solution of concentrated hydrochloric acid in a total of 4 L of water was added. The mixture was stirred for 30 minutes and then stirred for 3 hours in and ice-water bath giving a precipitate. The precipitate was isolated by filtration and washed with 1 L of cold 1:1 water/ethyl acetate and then 1 L of ethyl acetate. The precipitate was dried in a vacuum oven at between 45 and 50° C. under a nitrogen gas bleed for 24 hours, at 50°–55° C. for 24 hours and then at room temperature for 48 hours.

The dry precipitate was dissolved in approximately 9 L of boiling methanol. The solution was filtered and then distilled under vacuum to a volume of approximately 4 L. Reagent alcohol was added and the mixture was distilled under atmospheric pressure to a boiling point of between 72 and 74° C. and a total volume of approximately 5 L. The remaining mixture was stirred at room temperature for approximately 12 hours and then in an ice bath for 4 hours giving a precipitate. The precipitate was isolated by filtration and washed with approximately 1.5 L of alcohol. The isolated precipitate was dried by suction for 2 hours and then in a vacuum oven at between 55 and 60° C. under a nitrogen gas bleed for approximately 12 hours and the dry precipitate was passed through a size 10 clinical screen. Further drying in a vacuum oven at between 55 and 60° C. under a nitrogen gas bleed for 48 hours gave 1-(4-amino--5-chloro-2-methoxyphenyl)-5-piperidin-1-ylpentan-1-one hydrochloride (357 g, 0.99 mol), m.p. 220°–222° C.

Proceeding as in Example 14 but replacing piperidine with 4-methyl-piperidine gave 1-(4-amino-5-chloro-2-methoxyphenyl)-5-(4-methylpiperidin-1-yl-pentan-1-one hydrochloride, m.p. 197°–198° C.

Example 15

1-(4-Amino-5-chloro-2-methoxyphenyl)-5-piperidin-1-ylpentan-1-one

The following is the preparation of a compound of Formula I in which $R^1$ is chloro, $R^2$ is hydrogen, $R^3$ is methoxy and $R^4$ is a group of Formula (a), in which p is 0, n is 4 and $R^5$ and $R^6$ together are piperdin-1-yl.

A suspension of 5-(piperdin-1-yl)valeric acid hydrochloride (6.6 g, 30 mmol) in 100 mL of THF was cooled in an ice bath and 100 mL of 1N lithium bis(trimethylsilyl)amide in THF was added. The ice bath was removed and the resulting solution was stirred at room temperature for 1 hour. A mixture of methyl 2-methoxy-4-amino-5-chlorobenzoate (2.15 g, 10 mmol) and chlorotrimethylsilane (2.5 mL, 20 mmol) in 25 mL of THF was cooled in an ice bath and 20 mL of 1N lithium bis(trimethylsilyl)amide in THF was addled. The solution containing the 5-piperdin-1-ylvaleric acid and iN lithium bis(trimethylsilyl)amide was cooled in an ice bath and the mixture containing the methyl 2-methoxy-4-amino-5-chlorobenzoate was added over 5 minutes. The reaction mixture was removed from the ice bath and stirred at 50°–55° C. for 2 hours and then a solution of 25 mL of concentrated hydrochloric acid in 175 mL of water was added. The mixture was stirred at 50°–55° C. under a gentle stream of nitrogen and then 120 mL of ethyl acetate was added. The mixture was stirred in an ice bath for 1 hour giving a precipitate. The precipitate was isolated by filtration and washed with ethyl acetate. The precipitate was stirred in approximately 40 mL of boiling isopropanol for 30 minutes and then for 1 hour in an ice bath. The precipitate was isolated by filtration and washed with isopropanol. Drying in a vacuum oven at between 55 and 60° C. under a nitrogen gas bleed for 18 hours gave 1-(4-amino-5-chloro-2-methoxyphenyl)-5-piperidin-1-ylpentan-1-one hydrochloride (2.9 g, 8 mmol).

Example 16

The following are representative pharmaceutical formulations containing a compound of Formula I.

Oral Formulation

A representative solution for oral administration contains:

| | |
|---|---|
| Compound of Formula I | 100–1000 mg |
| Citric Acid Monohydrate | 105 mg |
| Sodium Hydroxide | 18 mg |
| Flavoring | |
| Water | q.s. to 100 mL |

Intravenous Formulation

A representative solution for intravenous administration contains:

| | |
|---|---|
| Compound of Formula I | 10–100 mg |
| Dextrose Monohydrate | q.s to make isotonic |
| Citric Acid Monohydrate | 1.05 mg |
| Sodium Hydroxide | 0.18 mg |
| Water for Injection | q.s. to 1.0 mL |

Tablet Formulation

A representative tablet form of a compound of Formula I may contain:

| | |
|---|---|
| Compound of Formula I | 1% |
| Microcrystalline cellulose | 73% |
| Stearic Acid | 25% |
| Colloidal Silica | 1% |

Example 17

Thoracic Esophagus 5-HT$_4$ Receptor Assay

The following describes an in vitro assay which utilizes rat isolated esophageal muscularis mucosae to identify test compounds which are 5-HT$_4$ receptor ligands.

Thoracic esophagi are isolated from male, Sprague-Dawley rats and placed in Tyrode's solution. The outer striated muscle is removed to reveal the muscularis mucosae. Each mucosae is suspended vertically in a 10 ml, tissue bath containing methysergide (1 µM), cocaine (30 µM), and corticosterone (30 µM) in Tyrode's solution maintained at 37° C. and constantly aerated with a 95% $O_2$ and 5% $CO_2$ gas mixture.

A resting tension of 1 g is applied to each tissue and thereafter 0.5 g is reapplied at 15 minute intervals. A steady state contraction to carbachol (3 µM) is produced and then the tissue is exposed to 5-HT in a cumulative-concentration fashion, increasing in concentration until maximal or near maximal relaxation is achieved. The 5-HT produces a concentration-dependent, 5-HT$_4$ receptor mediated relaxation of the muscularis mucosae tissue.

The tissue is exposed to drug free Tyrode's solution for 30 minutes and then again contracted with carbachol. The tissue is then exposed to test compound. If the test compound does not itself elicit relaxation of the esophageal muscularis mucosae, the tissue is exposed to 5-HT in the presence of the test compound. Compounds which intrinsically produce relaxation are characterized as $5\text{-}HT_4$ receptor agonists. Compounds which inhibit the relaxation responses to 5-HT are characterized as $5\text{-}HT_4$ receptor antagonists.

Proceeding as in Example 17, compounds of this invention were identified as $5\text{-}HT_4$ receptor ligands and characterized as $5\text{-}HT_4$ receptor agonists or $5\text{-}HT_4$ receptor antagonists.

Example 18

Prokinetic Assay

The following describes an in vivo method of determining prokinetic activity by measuring the extent the drug affects the rate of gastric emptying of test meal in rats. The method is that described by Droppleman et al., previously cited.

Test meal is prepared by slowly adding 20 g of cellulose gum (Hercules Inc., Wilmington, Del.) to 200 mL of cold distilled water that is being mixed in a Waring blender at approximately 20,000 rpm. Mixing continues until complete dispersion and hydration of the cellulose gum takes place (approximately 5 min). Three beef bouillon cubes are dissolved in 100 mL of warm water and then blended into the cellulose solution followed by 16 g of purified casein (Sigma Chemical Co., St. Louis, Mo.), 8 g of powdered confectioners sugar, 8 g of cornstarch, and 1 g of powdered charcoal. Each ingredient is added slowly and mixed thoroughly resulting in approximately 325 mL of a dark gray to black, homogenous paste. The meal is then refrigerated overnight during which time trapped air escapes. Prior to the assay the meal is removed from the refrigerator and allowed to warm to room temperature.

Mature (170 to 204 g) male Sprague-Dawley rats are deprived of food for 24 hours with water ad libitum. On the morning of the study each animal is weighed and randomly assigned to treatment groups consisting of ten animals per group. Each rat receives either vehicle, test compound or the reference standard metoclopramide by intraperitoneal injection. At 0.5 hours post injection 3.0 mL of test meal is orally administered to each rat with a 5.0 mL disposable syringe. Five test meal samples are weighed on an analytical balance and these weights are averaged to find a mean test meal weight. At 1.5 hours post injection each rat is sacrificed by carbon dioxide asphyxiation and the stomach is removed by opening the abdomen and carefully clamping and cutting the esophagus just below the pyloric sphincter. Taking care not to lose any of the its contents, each stomach is placed on a small, pre-weighed and correspondingly labeled 7 mL weigh boat and immediately weighed on an analytical balance. Each stomach is then cut open along the lesser curvature, rinsed with tap water, gently blotted dry to remove excess moisture and weighed. The amount of test meal remaining in the stomach is represented by the difference between the weight of the full stomach and the weight of the stomach empty. The difference between the amount of test meal remaining and the mean test meal weight represents the quantity of test meal that empties during the 1.5 hour post injection period.

Responses are represented as grams of meal emptied or percent change from control. Means and standard deviations of the test groups are compared to those of the reference groups. Significance is determined via Dunnett's t-test (Statistical Association Journal, December 1955, 1096–112).

Proceeding as in Example 18, compounds of this invention were determined to possess prokinetic activity.

Example 19

Anxiolytic Behavior Assay

The following describes an in vivo method for determining anxiolytic activity by measuring the extent the drug affects the natural anxiety of mice when exposed to a novel, brightly lighted environment.

Naive male C5BI/6J mice, 18–20 g, are kept in groups of 10 mice in quarters controlled for sound, temperature and humidity. Food and water are available ad libitum. The mice are kept on a 12 hour light and 12 hour dark cycle, with lights on at 6:00 a.m. and off at 6:00 p.m. All experiments begin at least 7 days after arrival on site.

The automated apparatus for detecting changes in exploration is obtained from Omni-Tech Electronics Columbus Ohio and is similar to that of Crawley and Goodwin (1980), as described in Kilfoil et al., cited previously. Briefly, the chamber consists of a plexiglass box (44×21×21 cm), divided into two chambers by a black plexiglass partition. The partition dividing the two chambers contains a 13×5 cm opening through which the mouse can easily pass. The dark chamber has clear sides and a white floor. A fluorescent tube light (40 watt) placed above the chambers provides the only illumination. The Digiscan Animal Activity Monitor System RXYZCM16 (Omni-Tech Electronics) records the exploratory activity of the mice within the test chambers.

Prior to commencement of the study the mice are given 60 min to acclimatize to the laboratory environment. After a mouse receives an intraperitoneal (i.p.) injection of either test compound or vehicle it is returned to its home cage for a 15 min post-treatment period. The mouse is then placed in the center of the light chamber and monitored for 10 minutes.

Anxiolysis is seen as a general increase in exploratory activity in the lighted area. An increase in exploratory activity is reflected by increased latency (the time for the mouse to move to the dark chamber when first placed in the center of the lighted area), increase in shuttle activity, increased or unaltered locomotor activity (number of grid lines crossed) and decreased time spent in the dark compartment.

Example 20

Withdrawal Anxiety Assay

The following describes an in vivo procedure for determining amelioration of the symptoms caused by withdrawal from addictive substances by measuring the extent the drug affects the anxiety that occurs in mice after chronically treating with an addictive substance and then abruptly ceasing the treatments.

Naive male BKW mice (25–30 g) are caged in groups of ten in quarters controlled for sound, temperature and humidity. Food and water are available ad libitum. The mice are kept on a 12 hour light cycle and 12 hour dark cycle, with lights on at 6:00 a.m. and off at 6:00 p.m. All experiments begin at least 7 days after arrival on site.

Levels of anxiety are determined by the two-compartment exploratory model of Crawley and Goodwin (see Example 19). Anxiolysis is seen as a general increase in exploratory activity in the lighted area. An increase in exploratory activity is reflected by increased latency (the time for the mouse to move to the dark chamber when first placed in the center of the lighted area), increased or unaltered locomotor activity (number of grid lines crossed), increased number of rears and decreased time spent in the dark compartment.

Increased exploratory activity in the lighted area is induced by treating the mice for 14 days with ethanol (8.0% w/v in drinking water), nicotine (0.1 mg/kg, i.p., twice daily) or cocaine (1.0 mg/kg, i.p., twice daily). Anxiolysis is assessed 1, 3, 7 and 14 days after commencement of the drug regime. The treatment is abruptly ceased and exploratory activity in the lighted area is determined 8, 24 and 48 hours thereafter. Vehicle or test compounds are administered during the withdrawal phase by intraperitoneal injection. Responses are represented as inhibition of the decrease in anxiolytic behavior after the ethanol, cocaine or nicotine treatment is ceased.

Example 21

Cognitive Enhancement Assay

The following describes a model to determine the cognitive enhancing activity by measuring the extent the test compound could alleviate the cognitive deficit induced by atropine (30 mg/kg, i.p.) using the Morris Water Maze.

Sprague Dawley rats (240–260 g) were kept in the laboratory the night prior to testing, and remained there throughout the experiment. The Morris Water Maze consists of a circular pool made from black plexiglass (122 cm diameter, 46 cm in height, with a 15 cm rim), filled with opaque water to a height of 35 cm. A hidden platform consisting of black plexiglass was placed 1–2 cm below the surface of the water. The pool was divided into four quadrants, arbitrarily corresponding to north, south, east and west. The platform was located in the south quadrant, about 24 cm from the side. Objects of high contrast were placed about the room to serve as spatial cues. A TV camera tracked the swim path of the rats, and the data thus obtained was examined to determine the time in seconds the rats took to find the platform (escape latency). Test trials were initiated by placing a rat into one of the four quadrants, facing the wall. Testing consisted of a block of six trials (starting first in the north quadrant, then east, south, west, north, and finally east) on each of two consecutive days. During each trial the rat was allowed 90 seconds to find the platform. When the rat successfully found the platform, it was given 30 seconds to "study" the spatial cues. When the rat failed to find the platform within 90 seconds, it was given a score of 90 seconds, and placed on the platform for 30 seconds.

The following groups of 8 rats each were used: 1) vehicle-treated controls; 2) atropine treated-controls; 3) atropine plus test drug. Thus the studies were designed to determine whether the test drug could alleviate the cognitive deficit induced by atropine (30 mg/kg, i.p.). Statistical tests were applied to test for heterogeneity of the learning curves, and separation of the learning curves.

Proceeding as in Example 21, compounds of this invention were determined to possess cognition enhancing properties.

While the present invention has been described with respect to specific embodiments thereof, it will be understood by those skilled in the art that various changes may be made and equivalents may be substituted without departing from the true spirit and scope of the invention. All such modifications are intended to be within the scope of the claims appended hereto.

We claim:

1. A compound of Formula I(b):

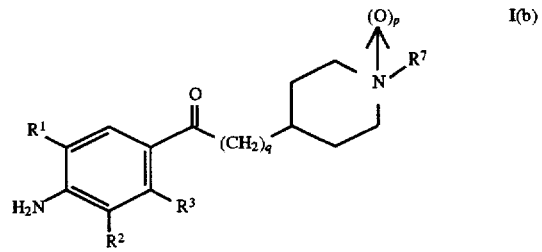

in which p is 0 or 1;

q is 2;

$R^1$ is chloro;

$R^2$ is hydrogen and $R^3$ is methoxy; and $R^7$ is hydrogen, $(C_{1-8})$alkyl, or $-(CH_2)_zR^{12}$ in which z is 2 or 3 and $R^{12}$ is hydroxy, $(C_{1-4})$alkyloxy, $-C(O)NR^{13}R^{14}$, $-NR^{13}C(O)R^{14}$, $-NR^{13}C(O)$ $OR_{14}$, $-SO_2NR^{13}R^{14}$, $-NR^{13}SO_2R^{14}$, $-NR^{13}SO_2NR^{14}R^{15}$ or $-NR^{13}C(O)NR^{14}R^{15}$ in which $R^{13}$, $R^{14}$ and $R^{15}$ are independently hydrogen, $(C_{1-4})$alkyl, trifluoromethyl or aryl; or a pharmaceutically acceptable salt thereof.

2. A compound of claim 1 in which p is 0 and $R^7$ is n-butyl, namely 1-(4-amino-5-chloro-2-methoxyphenyl)-3-[1-(n-butyl)piperidin-4-yl]propan-1-one or a pharmaceutically acceptable salt thereof.

3. The compound of claim 2 which is 1-(4-amino-5-chloro-2-methoxy-phenyl)-3-[1-(n-butyl)piperidin-4-yl] propan-1-one hydrochloride.

4. A compound of claim 1 in which p is 0 and $R^7$ is 2-[(methylsulfonyl)amino]ethyl, namely 1-(4-amino-5-chloro-2-methoxyphenyl)-3-{2-[(methylsulfonyl)amino] ethyl}piperidin-4-yl]propan-1-one or a pharmaceutically acceptable salt thereof.

5. The compound of claim 4 which is 1-(4-amino-5-chloro-2-methoxyphenyl)-3-{2-[(methylsulfonyl)amino] ethyl }piperidin-4-yl]propan-1-one hydrochloride.

6. A compound of Formula I(b):

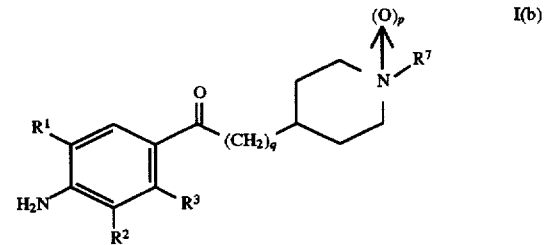

in which p is 0, q is 2, $R^1$ is chloro, $R^2$ is hydrogen, $R^3$ is methoxy, and $R^7$ is 3-(3, 4-dimethoxyphenyl)prop-1-yl, namely 1-(4-amino-5-chloro-2-methoxyphenyl)-3-{1-[3-(3, 4-dimethoxy-phenyl)prop-1-yl]piperidin-4-yl}propan-1-one or a pharmaceutically acceptable salt thereof.

7. The compound of claim 6 which is 1-(4-amino-5-chloro-2-methoxyphenyl)-3-{1-[3-(3,4-di-methoxyphenyl) prop-1-yl]-piperidin-4-yl}}propan-1-one hydrochloride.

8. A compound of Formula I(b):

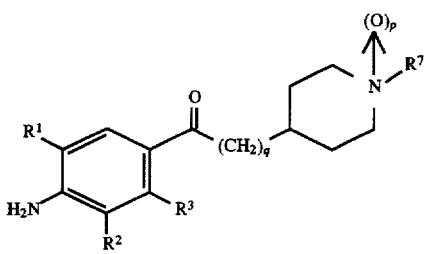

in which
p is 0 or 1;
q is 2;
$R^1$ is chloro;
$R^2$ and $R^3$ together are ethylenedioxy; and
$R^7$ is hydrogen, $(C_{1-8})$alkyl, $(C_{3-8})$alkenyl or phenyl$(C_{1-4})$alkyl (wherein the phenyl is optionally substituted with one to three substituents independently selected from $(C_{1-4})$alkyloxy, methylenedioxy, ethylenedioxy or halo) or $-(CH_2)_zR^{12}$ in which z is 2 or 3 and $R^{12}$ is hydroxy, $(C_{1-4})$alkyloxy, $-C(O)NR^{13}R^{14}$, $-NR^{13}C(O)R^{14}$, $-NR^{13}C(O)OR^{14}$, $-SO_2NR^{13}R^{14}$, $-NR^{13}SO_2R^{14}$, $-NR^{13}SO_2NR^{14}R^{15}$ or $-NR^{13}C(O)NR^{14}R^{15}$ in which $R^{13}$, $R^{14}$ and $R^{15}$ are independently hydrogen, $(C_{1-4})$alkyl, trifluoromethyl or aryl; or a pharmaceutically acceptable salt thereof.

9. A compound of claim 8 in which p is 0 and $R^7$ is 3-(4-methoxyphenyl)prop-1-yl, namely 1-(4-amino-5-chloro-2,3-ethylenedioxyphenyl)-3-{1-[3-(4-methoxyphenyl)prop-1-yl]-piperidin-4-yl}propan-1-one or a pharmaceutically acceptable salt thereof.

10. The compound of claim 9 which is [3-(4-methoxyphenyl)-prop-1-yl, namely] 1-(4-amino-5-chloro-2,3-ethylenedioxyphenyl)-3-{1-[3-(4-methoxyphenyl)-prop-1-yl]piperidin-4-yl}propan-1-one hydrochloride.

11. A pharmaceutical composition comprising a therapeutically effective amount of a compound of claim 1 in combination with at least one pharmaceutically acceptable excipient.

12. A pharmaceutical composition comprising a therapeutically effective amount of a compound of claim 2 in combination with at least one pharmaceutically acceptable excipient.

13. A pharmaceutical composition comprising a therapeutically effective amount of a compound of claim 4 in combination with at least one pharmaceutically acceptable excipient.

14. A pharmaceutical composition comprising a therapeutically effective amount of a compound of claim 6 in combination with at least one pharmaceutically acceptable excipient.

15. A pharmaceutical composition comprising a therapeutically effective amount of a compound of claim 8 in combination with at least one pharmaceutically acceptable excipient.

16. A pharmaceutical composition comprising a therapeutically effective amount of a compound of claim 9 in combination with at least one pharmaceutically acceptable excipient.

17. A method for treating a urinary tract disorder in an animal in need of such treatment, which method comprises administering to such an animal a therapeutically effective amount of a compound of claim 1.

18. A method for treating a urinary tract disorder in an animal in need of such treatment, which method comprises administering to such an animal a therapeutically effective amount of a compound of claim 2.

19. A method for treating a urinary tract disorder in an animal in need of such treatment, which method comprises administering to such an animal a therapeutically effective amount of a compound of claim 4.

20. A method for treating a urinary tract disorder in an animal in need of such treatment, which method comprises administering to such an animal a therapeutically effective amount of a compound of claim 6.

21. A method for treating a urinary tract disorder in an animal in need of such treatment, which method comprises administering to such an animal a therapeutically effective amount of a compound of claim 8.

22. A method for treating a urinary tract disorder in an animal in need of such treatment, which method comprises administering to such an animal a therapeutically effective amount of a compound of claim 9.

* * * * *